(12) United States Patent
Grillo et al.

(10) Patent No.: US 6,468,561 B1
(45) Date of Patent: *Oct. 22, 2002

(54) AQUEOUS FILM COATING WITH IMPROVED PROPERTIES

(75) Inventors: Susan M. Grillo, Quakertown; Rita M. Steffenino, Harleysville; Stuart C. Porter, Hatfield; Edward J. Woznicki, Douglassville; David K. Isganitis, East Greensville, all of PA (US)

(73) Assignee: BPSI Holdings, Inc., Wilmington, DE (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/886,731
(22) Filed: Jun. 30, 1997

Related U.S. Application Data

(63) Continuation of application No. 08/593,112, filed on Feb. 1, 1996, now abandoned, which is a continuation of application No. 08/151,611, filed on Nov. 12, 1993, now abandoned, which is a continuation of application No. 07/810,215, filed on Dec. 19, 1991, now abandoned, which is a continuation of application No. 07/306,769, filed on Feb. 3, 1989, now abandoned, which is a continuation-in-part of application No. 06/876,186, filed on Jun. 19, 1986, now Pat. No. 4,802,924.

(51) Int. Cl.[7] .................................................. A61K 9/36
(52) U.S. Cl. ...................................... 424/480; 424/479
(58) Field of Search ........................................... 424/490

(56) References Cited

U.S. PATENT DOCUMENTS

| | | | | |
|---|---|---|---|---|
| 3,421,920 A | * | 1/1969 | Shetty et al. | |
| 3,766,165 A | * | 10/1973 | Rennhard et al. | 426/152 |
| 3,876,794 A | * | 4/1975 | Rennhard et al. | 260/209 |
| 4,543,370 A | * | 9/1985 | Porter et al. | 523/100 |
| 4,610,891 A | * | 9/1986 | Miyamoto | 427/3 |
| 4,622,233 A | * | 11/1986 | Torres | 426/548 |
| 4,802,924 A | * | 2/1989 | Woznicki et al. | 427/3 |
| 4,834,985 A | * | 5/1989 | Elger et al. | 424/488 |
| 5,411,746 A | * | 5/1995 | Signorino et al. | 424/480 |

OTHER PUBLICATIONS

Pfizer Polydextrose 1985.*
Pfizer Polydextrose Bulletin 1985.*
Story of Sugars Corn Products Co.*
"The Story of Sugars" Corn Products Co.*

* cited by examiner

*Primary Examiner*—Thurman K. Page
*Assistant Examiner*—Humera N. Sheikh
(74) *Attorney, Agent, or Firm*—John F. A. Earley; John F. A. Earley III; Harding, Earley, Follmer & Frailey

(57) ABSTRACT

Providing a film coating on solid forms such as pharmaceutical tablets, foods, confectionery forms, seeds for agriculture, and the like by coating them with polydextrose, or a combination of polydextrose and another polymer, or a layer of polydextrose overcoated by a layer of another polymer.

55 Claims, 25 Drawing Sheets

Tablet coated with standard HPMC formula film coating (15% solids level)

Photograph 1: Tablet coated with standard HPMC formula film coating (15% solids level)

Photograph 2: Tablet coated with modified HPMC formula film coating (23% solids level)

Photomicrograph A: HPMC Formula Film Coating

Photomicrograph B: HPMC/Polydextrose Formula Film Coating

Photomicrograph C: HPMC/HPC Formula Film Coating

Photomicrograph D: HPMC/HPC/Polydextrose Formula Film Coating

Photomicrograph E: HPC Formula Film Coating

Photomicrograph F: HPC/Polydextrose Formula Film Coating

Photomicrograph G: AQUACOAT Formula Film Coating

Photomicrograph H: AQUACOAT/Polydextrose Formula Film Coating

Photomicrograph I: Water-Soluble Cellulose Acetate Formula Film Coating

Photomicrograph J: Water Soluble Cellulose Acetate/
Polydextrose Formula Film Coating Photomicrograph K: HPMC Formula Film Coating (3% weight gain)

Photomicrograph L: HPMC/Polydextrose Formula Film Coating
(3% weight gain)

Photomicrograph M: HPMC Formula Film Coating (6% weight gain)

Photomicrograph N: HPMC/Polydextrose Formula Film Coating (6% weight gain)

AQUEOUS FILM COATING WITH IMPROVED PROPERTIES

This is a continuation of application Ser. No. 08/593,112 filed on Feb. 1, 1996 now abandoned which is a continuation of Ser. No. 08/151,611 filed on Nov. 12, 1993, which is a continuation of Ser. No. 07/810, 215 filed on Dec. 19, 1991 abandoned, which is a continuation of Ser. No. 07/306,769 filed on Feb. 3, 1989 abandoned, which is a continuation-in-part of Ser. No. 07/876,186 filed on Jun. 19, 1986, now U.S. Pat. No. 4,802,924.

This invention is in the field of aqueous film coating of solid forms such as pharmaceutical products, food products, confectionery products, and seeds for agriculture, and is more specifically concerned with providing such coatings based on polydextrose.

BACKGROUND OF THE INVENTION

Cellulose polymers such as hydroxypropyl nethylcellulose have long been recognized in the art as being suitable for the aqueous film coating of pharmaceutical tablets and the like.

While it is normally possible to produce excellent film coatings with such cellulosic materials, difficulties can sometimes arise with respect to the ability of the resultant film coatings to adhere satisfactorily to the surface to which they are applied. This is especially true when considering tablet substrates such as waxy matrix sustained release products and multi-vitamin products (with which the phenomenon of "bridging" of the coating across debossed legends can be a substantial problem).

It is also desirable to be able to produce film coatings for food and confectionery products which are able to replace the currently used sugar coatings, in order to meet the requirements for low calorie, non-cariogenic (that is, not harmful to teeth) coatings for such products.

While cellulosic polymers can meet these requirements, they tend to produce coatings that have undesirable taste and mouth-feel (that is, they are somewhat bitter and slimy in texture; both undesirable features especially for confectionery products).

SUMMARY OF THE INVENTION

Aqueous film coatings based on the polymer polydextrose provide the solution to both the pharmaceutical, and the food and confectionery problems described. Used alone, or in combination with other polymers, polydextrose produces pharmaceutical film coatings that exhibit excellent adhesive qualities, while when used in food and confectionery applications, it can produce coatings with good organoleptic properties that are low calorie and non-cariogenic in nature.

Aqueous film coatings based on the polymer polydextrose are useful on various grains and seeds since such coatings facilitate handling of the grains and seeds. For example, some automatic planting machines do not effectively manipulate seeds that are tiny in size, and coating such seeds with the inventive coating creates a larger volume that is more easily handled by the automatic planting machines. Further, the inventive coating maintains the germinative properties of the seeds.

One characteristic of polydextrose, however, is that it has an extremely low average molecular weight value (for example, peak molecular weight, $M_p$, is approximately 1230). It is well known that low molecular weight polymers produce extremely weak films. Rowe ("Molecular Weight Studies on Hydroxypropyl Methylcellulose Phthalate" *Acta-Pharm. Technologica* 28 (2), p. 129 1982) has stated that for the purposes of film coating, there exists a CRITICAL MOLECULAR WEIGHT value for polymers such as hydroxypropyl methylcellulose (H.P.M.C.), below which there is a great risk of the coating cracking. For H.P.M.C., he stated that the $M_p$ value, which is indicative of the molecular weight of the main component, is approximately $8.0 \times 10^4$.

This value for HPMC is significantly greater than the $M_p$ value for polydextrose, which would thus not be expected to produce satisfactory film coatings.

Additionally, Osterwald ("Properties of Film-Formers and Their Use in Aqueous Systems", *Pharm. Res.*, 1985, p. 15) has stated that for film coating, polymers producing solutions (containing 2% w/w of the polymer in water) having viscosities in the range of 3–15 mPas (milli Pascal seconds) (same as centipoise numerically) ought to be used, and that below this range, the polymer chains shorten to such an extent that the stability of the film is affected (i.e. film strength decreases too much). Two percent aqueous solutions of polydextrose have a viscosity of less than 2 mPas (in fact the value is too low to be differentiated from that of plain water).

Consequently, to those skilled in the art, polydextrose would be considered to produce film coatings that are entirely unsuitable for modern film coating processes; yet we have found it can produce excellent film coatings that in some cases have superior properties to those obtained from more traditional polymers.

Finally, polydextrose can be formulated into a dry-edible film coating composition, shipped to the user and mixed easily into water to form an aqueous coating suspension.

The polydextrose aqueous coating suspension comprises an effective amount of polydextrose, plasticizer, detackifier, and a secondary film former, mixed into water to form an aqueous coating suspension which may be applied to the forms to be coated, as by spraying. Optionally, a colorant may be added to the aqueous coating suspension before the coating step. Also, other polymers, such as maltodextrin and cellulosic, vinylic, and acrylic polymers, may be used in combination with polydextrose. For example, a cellulosic polymer, such as hydroxypropyl methylcellulose, may be substituted for the secondary film former, and the resulting formula is particularly adapted for coating waxy matrix tablets, which are particularly difficult to coat. All ingredients of the coating suspension are edible and suitable for ingestion.

The film former of the coating is polydextrose, or a mixture of polydextrose and one or more other polymers, such as a cellulosic polymer film former.

Also, it may be advantageous to coat with a layer of polydextrose aqueous coating suspension, and then overcoat with a layer of another polymer coating suspension such as a cellulosic film polymer coating suspension.

Other polymers that may be used with polydextrose may be maltodextrin, vinylic polymers, acrylic polymers and cellulosic polymers. The acrylic polymer may be an acrylic latex. The cellulosic film polymer may be hydroxypropyl methylcellulose, hydroxypropyl cellulose, pseudolatex ethylcellulose, or water-soluble cellulose acetate.

The plasticizer may be polyethylene glycol, triacetin, propylene glycol, acetyltriethyl citrate, dibutyl sebacate, or glycerine.

The colorants may be FD&C lakes, D&C lakes, titanium dioxide, or dyes approved for ingestion by the U.S. Federal Drug Administration. Examples of such pigments are listed in Colorcon U.S. Pat. No. 4,543,370 issued Sep. 24, 1985, and incorporated herein by reference.

The detackifier may be lecithin or mineral oil.

The secondary film former may be sodium alginate or propylene glycol alginate.

With some polymer coatings, such as polydextrose/EUDRAGIT formula coatings, an antifoaming agent (such as AEROSOL OT, 75%) and a lubricating aid (such as magnesium stearate) may be added to the formula.

The polydextrose based coating is especially effective in coating tablets and the like having debossed or intaglio logos, trademarks, designs or words thereon since it adheres to the tablet surfaces without bridging and obscuring the debossed or intaglio printing.

DETAILED DESCRIPTION

Figure 1:
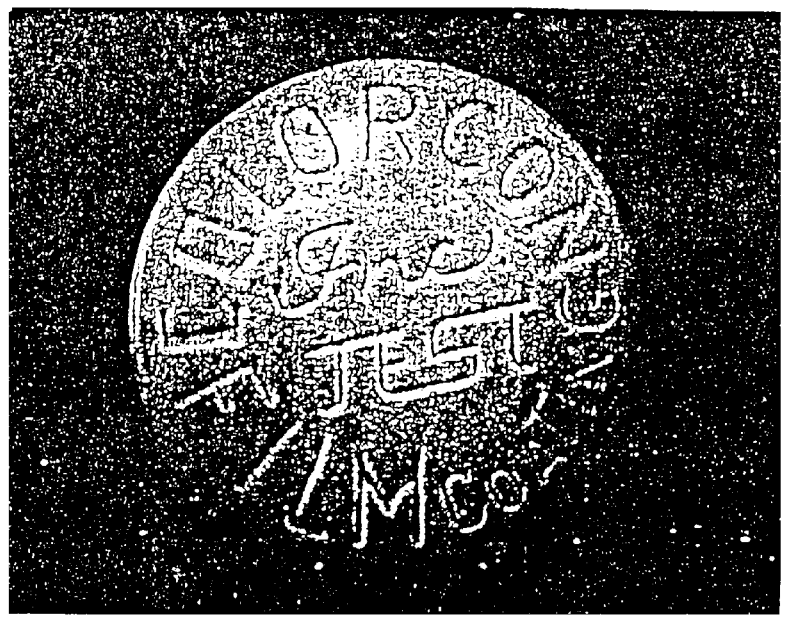
FIG. 1 shows a tablet coated with a standard HPMC formula film coating (15% solids level).
Figure 2:
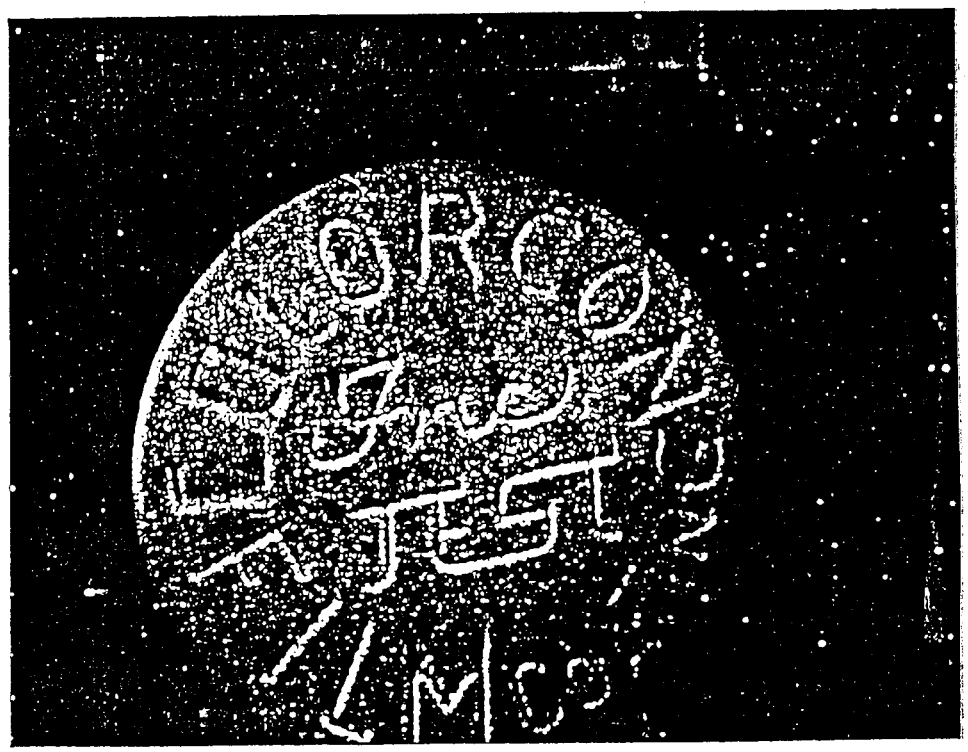
FIG. 2 shows a tablet coated with a modified HPMC formula film coatin (23% solids level).

We now turn to the examples of the invention, all of which disclose formulations which may be mixed into water to form an aqueous coating suspension that may be effective to coat pharmaceuticals, food, confectioneries, and seeds for agriculture.

This invention is concerned with coating solid forms such as seeds for agriculture, and pharmaceutical, confectionery and food forms including medicinal tablets, vitamin tablets, aspirin tablets, capsules, chewing gum balls, chocolates, pieces of candy, almonds, breakfast cereal, and the like.

EXAMPLES

The following examples illustrate the invention. All units and percentages used herein are by weight.

Example 1

A clear coating suspension is made for coating chocolates by mixing the following ingredients into water to form an aqueous coating solution.

|  | % | Grams |
| --- | --- | --- |
| Polydextrose | 81.42 | 2050 |
| Soda Ash | 0.72 | 18.2 |
| Kelgin LV | 4.96 | 125 |
| Alcolec F-100 | 2.98 | 75 |
| Triacetin | 4.96 | 125 |
| PEG 8000 | 4.96 | 125 |

Polydextrose is made by Pfizer, Inc., Kelgin LV is sodium alginate made by the Kelco division of Merck and is used as a secondary film former, Alcolec F-100 is water miscible lecithin made by the American Lecithin Co. and is used as a detackifier in the formula, triacetin is triethyl citrate by Pfizer and is used as a plasticizer and PEG 8000 is polyethylene glycol 8000 and is used in the formula as a plasticizer.

The mixing procedure is to mix 300 grams of the dry ingredients into about 1700 milliliters of water to make an aqueous coating.

The chocolates to be coated are placed in a 24 inch Accela Cota coating pan with 4 anti-skid bars, and the aqueous coating suspension is sprayed onto the chocolates. During the coating procedure, the inlet air is 45° C., the outlet air is 30° C., the atomizing air is 3 bar, the pan speed is 12 rpm, the feed rate is 18 grams/minute, and the coating time is 90 minutes. The procedure produced a very nice coating on the chocolates with no tack, and with no slimy taste.

Example 2

In order to coat vitamin tablets, a formula having the following ingredients is dry mixed together and then mixed into water to form an aqueous coating suspension which is sprayed onto the vitamin tablets:

|               | %     | Grams  |
|---------------|-------|--------|
| Polydextrose  | 68.38 | 492.3  |
| Kelgin LV     | 4.18  | 30.1   |
| Alcolec F-100 | 2.51  | 18.1   |
| Triacetin     | 2.09  | 15.0   |
| PEG 8000      | 6.27  | 45.1   |
| R-40 lake     | 12.50 | 90.0   |
| TiO$_2$       | 4.00  | 28.8   |
|               |       | 720.0  |
| H$_2$O        |       | 4080.0 |
|               |       | 4800.0 |

The R-40 lake is FD&C Red number 40 aluminum lake made by Colorcon, West Point, Pa.

The mixing procedure is to blend all dry ingredients into a blender for about 5 minutes, and add triacetin and blend for an additional 5 minutes. Then the formula is mixed into 4080 milliliters of distilled water to form an aqueous coating solution.

A 24 inch Accela Cota coating pan is loaded with 11 kilograms of vitamin tablets which have a debossed or intaglio logo on them. The spray coating parameters are inlet air 85° C., outlet air 50° C., atomizing air 3 bar, pan speed 12 rpm, feed rate 60 grams/minute, and coating time 80 minutes. The vitamin tablets receive a very nice coating with a good logo with no bridging, and no tack.

Example 3

It is desired to color gumballs and for this purpose the following formula is dry mixed together and is mixed into water to make an aqueous coating suspension which is sprayed onto the gumballs.

|                   | %    | Grams |
|-------------------|------|-------|
| Polydextrose      | 70.0 | 210.0 |
| PEG 400           | 2.5  | 7.5   |
| Sodium Alginate MV| 5.0  | 15.0  |
| TiO$_2$           | 10.0 | 30.0  |
| Alcolec F-100     | 2.5  | 7.5   |
| Y-5 HT lake       | 10.0 | 30.0  |

The Y-5 HT lake is FD&C Yellow number 5 aluminum lake made by Colorcon, West Point, Pa. The solids of this aqueous coating suspension amount to 300 grams and the water amounts to 1700 grams, so the suspension is about 15% solids. In spray coating the gumballs, the inlet air is 66° C., the outlet air is 35° C., the atomizing air is 3 bar, the feed rate is 30 grams/minute, the pan speed is 18 rpm, and the coating time is 45 minutes.

Example 4

Instead of coating the gumballs with a lake formula as in Example 3, it is desired to coat the gumballs with a dye formula, and the following formula is mixed into water to form an aqueous coating suspension which is sprayed onto the gumballs.

|                   | %    | Grams |
|-------------------|------|-------|
| Polydextrose      | 79.5 | 238.5 |
| PEG 400           | 2.5  | 7.5   |
| Sodium Alginate MV| 5.0  | 15.0  |
| TiO$_2$           | 10.0 | 30.0  |
| Alcolec F-100     | 2.5  | 7.5   |
| Y-5 Dye           | 0.5  | 1.5   |

The Y-5 dye is FD&C Yellow number 5 dye approved by the U.S. Federal Drug Administration for ingestion, the solids content amounts 300 grams, and the water content of the aqueous coating suspension is 1700 grams, the suspension being about 15% solids. The air, feed rate, and pan speed parameters of the spraying are the same as in Example 3 except the coating time is 50 minutes.

Example 5

It is desired to coat almonds with a cherry color, and the following formula is mixed together and into an aqueous suspension and sprayed onto the almonds.

|                          | %     | Grams   |
|--------------------------|-------|---------|
| Polydextrose             | 68.47 | 1711.75 |
| Sodium Alginate (Kelgin LV) | 4.18 | 104.50 |
| Alcolec F-100            | 2.51  | 62.75   |
| Triacetin                | 4.18  | 104.50  |
| PEG 8000                 | 4.18  | 104.50  |
| R-40 HT lake             | 13.39 | 334.75  |
| Y-6 HT lake              | 3.11  | 77.75   |

The sodium alginate is a secondary film former that gives the resulting coating a glossy appearance. The R-40 HT lake is FD&C Red number 40 aluminum lake, and the Y-6 HT lake is FD&C Yellow number 6 aluminum lake, both made and sold by Colorcon, West Point, Pa. The formula, 240 grams, is mixed into 960 milliliters of water, and the resulting aqueous coating suspension is spray coated onto the almonds in a coating pan. The almonds may have previously been given a subcoat of the clear polydextrose formula of Example 1, by spraying the Example 1 aqueous coating suspension onto the almonds with inlet air 73° C., outlet air 48° C., atomizing air 45 psi, pan speed 12 rpm, feed rate 34 grams/minute, and coating time 35 minutes.

To apply the cherry color to the almonds, the almonds are placed in a coating pan and the cherry color aqueous coating suspension is sprayed onto the almonds as they are being rotated in the pan, with the inlet air being 73° C., the outlet air being 48° C., the atomizing air being 45 psi, the pan speed being 12 rpm, and the feed rate being 40 grams/minute, and the coating time being 30 minutes.

Example 6

It is desired to coat KIX breakfast cereal with polydextrose, and the following formula is mixed into an aqueous suspension which is sprayed onto the KIX cereal puffs in a fluidized bed coater, such as made by Aeromatic.

| | % | Grams |
|---|---|---|
| Polydextrose | 71.00 | 16.05 |
| PEG 400 | 2.26 | 0.51 |
| Kelgin LV | 4.52 | 1.02 |
| Alcolec F-100 | 2.26 | 0.51 |
| $TiO_2$ | 10.00 | 2.26 |
| Y-5 HT lake | 10.00 | 2.26 |
| | | 22.60 |
| $H_2O$ | | 277.5 |

The procedure is to partly fill the bed coater cone with KIX cereal puffs, and turn on the coater to support the puffs in the air, and spray the puffs with the aqueous suspension. The inlet temperature is 80° C., the outlet temperature is 38° C., the feed rate is 10 grams/minute, and the air is 1 bar.

Example 7

Polydextrose may be combined with a cellulosic polymer, such as Methocel E5, to obtain the superior adhesiveness of the polydextrose and the superior moisture barrier of the cellulosic polymer in coating vitamin tablets. An example of a formula is as follows.

| | % | Grams |
|---|---|---|
| Polydextrose | 34.24 | 246.5 |
| Methocel E5 | 34.24 | 246.5 |
| Kelgin LV | 4.18 | 30.1 |
| Alcolec F-100 | 2.51 | 18.1 |
| Triacetin | 2.09 | 15.0 |
| PEG 8000 | 6.27 | 45.1 |
| Y-5 HT lake | 12.50 | 90.0 |
| $TiO_2$ | 4.00 | 28.8 |

The Y-5 HT lake is FD&C Yellow number 5 lake made by Colorcon, West Point, Pa. The formula contains 720 grams of solids and is mixed into 4080 milliliters of water to give a total weight of the aqueous coating suspension of 4800 grams. Methocel E-5 is hydroxypropyl methyl cellulose made by Dow Chemical Co. The aqueous coating suspension is sprayed onto tablets in a coating pan with inlet air at 85° C., outlet air at 50° C., atomizing air 3 bar, pan speed 12 rpm, feed rate 53 grams/minute, and coating time 90 minutes.

Example 8

Another example of a formula particularly adapted for applying a coating to vitamin tablets with intaglio logos without bridges comprises a 75% to 25% ratio of polydextrose to Methocel E-5, instead of the 50% to 50% ratio shown in Example 7, and is listed below.

| | % | Grams |
|---|---|---|
| Polydextrose | 51.36 | 369.8 |
| Methocel E-5 | 17.12 | 123.3 |
| Kelgin LV | 4.18 | 30.1 |
| Alcolec F-100 | 2.51 | 18.1 |
| Triacetin | 2.09 | 15.0 |
| PEG 8000 | 6.27 | 45.1 |

-continued

| | % | Grams |
|---|---|---|
| Y-6 HT lake | 12.50 | 90.0 |
| $TiO_2$ | 4.00 | 28.8 |

Example 9

Another example of a formula containing a mixture of polydextrose and a cellulosic polymer for coating vitamin tablets is:

| | % | Grams |
|---|---|---|
| Polydextrose | 51.36 | 369.8 |
| Klucel EF | 17.12 | 123.3 |
| Kelgin LV | 4.18 | 30.1 |
| Alcolec F-100 | 2.51 | 18.1 |
| Triacetin | 2.09 | 15.0 |
| PEG 8000 | 6.27 | 45.1 |
| Y-6 HT lake | 12.50 | 90.0 |
| $TiO_2$ | 4.00 | 28.8 |

Klucel EF is hydroxypropyl cellulose by Hercules, Inc.

Example 10

Another example of a formula containing both polydextrose and a cellulosic polymer is as follows.

| | % | Grams |
|---|---|---|
| Polydextrose | 61.60 | 443.50 |
| Klucel EF | 6.80 | 48.96 |
| Kelgin LV | 4.18 | 30.10 |
| Alcolec F-100 | 2.51 | 18.10 |
| Triacetin | 2.09 | 15.00 |
| PEG 8000 | 6.26 | 45.10 |
| R-40 HT lake | 6.25 | 45.00 |
| Y-6 HT lake | 6.25 | 45.00 |
| $TiO_2$ | 4.06 | 29.23 |

Example 11

Another formula containing a mixture of polydextrose and hydroxypropyl methyl cellulose is as follows.

| | % | Grams |
|---|---|---|
| Polydextrose | 36.86 | 921.5 |
| Methocel E-5 | 36.86 | 921.5 |
| Kelgin LV | 4.50 | 112.5 |
| Alcolec F-100 | 2.70 | 67.5 |
| Triacetin | 2.25 | 56.3 |
| PEG 8000 | 6.75 | 168.8 |
| $TiO_2$ | 9.32 | 233.0 |
| B-1 lake | 0.76 | 19.0 |

The B-1 lake is FD&C Blue number 1 aluminum lake. This formula is especially advantageous if it is desired to coat waxy matrix tablets, such as Dimetaps by A. H. Robbins, which are very hard to coat because it is difficult to get anything to adhere to their waxy surface.

The formula ingredients are mixed into sufficient water to make a 15% solids suspension, and the suspension is sprayed onto waxy matrix tablets at 45° C. inlet air, 30° C. outlet air, 3 bar atomizing air, 44 grams/minute feed rate, and 12 rpm pan speed.

Example 12

The outer surface of gumballs may be very rough with a large number of holes, and it may be desirable to apply a subcoat and fill in the holes before applying the thin coating of polydextrose as in Example 1, for example. A suitable subcoat may be made from the following formula into an aqueous coating suspension and sprayed onto the gumballs.

|  | % | Grams |
| --- | --- | --- |
| Polydextrose | 52.2 | 208.8 |
| PEG 400 | 1.8 | 7.2 |
| Sodium Alginate | 7.0 | 28.0 |
| Titanium Dioxide | 7.0 | 28.0 |
| Alcolec F-100 | 2.1 | 8.4 |
| Avicel 105 microcrystalline cellulose | 30.0 | 120.0 |
| PEG 400 is polyethylene glycol 400. | | |

Example 13

Another formula for coating chocolates, an orange color, is as follows.

|  | % | Grams |
| --- | --- | --- |
| Polydextrose | 68.81 | 206.4 |
| Kelgin LV | 4.18 | 12.5 |
| Alcolec F-100 | 2.15 | 6.5 |
| Triacetin | 4.18 | 12.5 |
| PEG 8000 | 4.18 | 12.5 |
| Red 40 lake | 13.39 | 40.2 |
| Y-6 lake | 3.11 | 9.3 |

Example 14

Vitamin tablets are spray coated in a coating pan with an aqueous coating suspension of Example 1 with the inlet air 85° C., outlet air 50° C., atomizing air 3 bar, pan speed 12 rpm, feed rate 60 grams/minute, and coating time 80 minutes.

Then the polydextrose coated vitamin tablets are spray coated with an OPADRY coating suspension made in accordance with the disclosure in Colorcon U.S. Pat. No. 4,543,370 which issued Sep. 24, 1985, which is incorporated herein by reference.

Example 15

A comparison of adhesion values is made between a film coating having a standard HPMC formula and a film coating having a modified HPMC formula having polydextrose, and the formulas for each are as follows:

Standard Hydroxypropyl Methylcellulose (HPMC) Formula

|  | % | Grams |
| --- | --- | --- |
| HPMC E-5 | 61.36 | 18.40 |
| Titanium Dioxide | 29.70 | 8.91 |

-continued

Standard Hydroxypropyl Methylcellulose (HPMC) Formula

|  | % | Grams |
| --- | --- | --- |
| PEG 400 | 6.35 | 1.91 |
| FD&C Yellow No. 6, HT, 39% | 1.94 | 0.58 |
| D&C Yellow No. 10, HT, 17% | 0.65 | 0.20 |

Modified HPMC Formula

|  | % | Grams |
| --- | --- | --- |
| HPMC E-5 | 38.28 | 11.48 |
| Polydextrose Powder | 23.08 | 6.92 |
| Titanium Dioxide | 29.70 | 8.91 |
| PEG 400 | 6.35 | 1.91 |
| FD&C Yellow No. 6, HT, 39% | 1.94 | 0.58 |
| D&C Yellow No. 10, HT, 17% | 0.65 | 0.20 |

The film Coatings are coated onto placebos having the following substrate formula:

|  | % | Kilograms |
| --- | --- | --- |
| Starch 1500 | 49.75 | 120.00 |
| Microcrystalline Cellulose (Avicel 101) | 49.75 | 120.00 |
| CAB-O-SIL EH-5 | 0.249 | 0.60 |
| Magnesium Stearate | 0.249 | 0.60 |

The microcrystalline cellulose is Avicel 101 made by FMC Corporation, and STARCH 1500 is a physically modified corn starch excipient made by the Colorcon division of Berwind Pharmaceutical Services, Inc., West Point, Pa.

The CAB-O-SIL is a glident and anti-adherent that improves flow properties, and is made by Cabot Corporation. The magnesium stearate acts as a tablet lubricant and is made by Mallinckrodt.

To obtain the placebo mix, the STARCH 1500 starch excipient, Avicel 101 microcrystalline cellulose, and CABO-O-SIL are blended together for nine minutes in a PK blender having an I-bar. The magnesium stearate is added to the mixture and the mixture is blended for another minute (no I-bar).

The placebo mix is tableted into flat-faced ⅜ inch round placebos using a Manesty 16 Station Betapress rotary tablet machine made by Manesty Machines Limited, Liverpool, England.

The mixing procedure for each film coating is to blend all dry ingredients together for approximately 30 seconds, and add the liquid ingredient of the formula and blend for an additional 30 seconds. Then, 30 grams of the blended formula is mixed into about 170 grams of distilled water for 30 minutes (or until well dispersed) to make an aqueous coating.

The placebos are sprayed in an AEROMATIC spraying apparatus, made by Aeromatic, Inc., Towaco, N.J., at 15% solids and 3% weight gain. During the coating procedure, the inlet air is 60° C., the outlet air is 40° C., the atomizing air is 3 bar, and the feed rate is 10–12 milliliters/minute. The charge is 1000 grams of placebos.

Adhesion testing of the film coatings is made in an MTS Tensile Tester. In the adhesion test, the peak force required to cause complete detachment of the coating from its substrate is measured, with adhesion values expressed as this peak force per unit area of tablet surface.

$$\text{Film Adhesion (kPa)} = \frac{\text{Load (N)}}{(\text{Surface Area of Tablets})(0.001)}$$

Where Load=Highest Amount of Force Required To Remove Film From Substrate kPa (Kilopascal): SI Metric Unit of Pressure (N/Square Meter)

N (Newtons): SI Metric Unit of Force 0.001=Conversion Factor

The adhesion value for the modified HPMC formula having polydextrose is 441.03 (±33.86) kPa, whereas the adhesion value for the standard HPMC formula is only 371.33 (±18.48) kPa. (The "±" values represent standard deviations of the average adhesion value of all tablets tested.)

Example 16

Another comparison of adhesion values is made using the procedures of Example 15, except a hydrophobic substrate is substituted for the microcrystalline cellulose/STARCH 1500 substrate of Example 15. The hydrophobic substrate comprises 99.0% directly compressible dicalcium phosphate (EM-COMPRESS made by Edward Mendell Company, Inc.) and 1.0% magnesium stearate, and is made by blending the dicalcium phosphate and magnesium stearate together for 15 minutes in PK blender (no I-bar). The resulting mix is tableted into flat-faced ⅜ inch round placebos using a Manesty 16 Station Betapress rotatary tablet machine.

The adhesion values for the modified HPMC formula having polydextrose is 84.26 (±13.55) kPa, whereas the adhesion value for the standard HPMC formula is only 53.22 (±9.05) kPa.

Example 17

Another comparison of adhesion values is made using the procedures of Example 16, except a non-polydextrose-based film coating having the following standard HPC formula is compared with a polydextrose-based film coating having the following modified HPC formula having polydextrose:

| Standard Hydroxypropyl Cellulose (HPC) Formula | | |
|---|---|---|
| | % | Grams |
| Klucel EF | 61.36 | 18.40 |
| Titanium Dioxide | 29.70 | 8.91 |
| PEG 400 | 6.35 | 1.91 |
| FD&C Yellow No. 6, HT, 39% | 1.94 | 0.58 |
| D&C Yellow No. 10, HT, 17% | 0.65 | 0.20 |

| Modified HPC Formula | | |
|---|---|---|
| | % | Grams |
| Klucel EF | 38.27 | 11.48 |
| Polydextrose Powder | 23.08 | 6.92 |
| Titanium Dioxide | 29.70 | 8.91 |
| PEG 400 | 6.35 | 1.91 |
| FD&C Yellow No. 6, HT, 39% | 1.94 | 0.58 |
| D&C Yellow No. 10, HT, 17% | 0.65 | 0.20 |

The adhesion value for the modified HPC formula having polydextrose is 316.73 (±25.24) kPa. However, the adhesion value for the standard HPC formula is only 217.13 (±30.87) kPa.

Example 18

Another comparison of adhesion values is made using the procedure of Example 16, except a film coating having the following standard AQUACOAT formula is compared with a film coating having the following modified AQUACOAT formula having polydextrose:

| Standard AQUACOAT Formula | | |
|---|---|---|
| | % | Grams |
| AQUACOAT (30% w/w) | 30.78 | 9.23 (dry solids) (30.77 grams as a solution) |
| HPMC E-5 (19% w/w) | 30.78 | 9.23 (dry solids) (48.60 grams as a solution) |
| Dibutyl Sebacate | 6.14 | 1.85 |
| Titanium Dioxide | 29.71 | 8.91 |
| FD&C Yellow No. 6, HT, 38% | 1.94 | 0.58 |
| D&C Yellow No. 10, HT, 15% | 0.65 | 0.20 |

| Modified AQUACOAT Formula | | |
|---|---|---|
| | % | Grams |
| AQUACOAT (30% w/w) | 26.23 | 7.87 (dry solids) (26.22 grams as a solution) |
| HPMC E-5 (19% w/w) | 26.23 | 7.87 (dry solids) (41.42 grams as a solution) |
| Polydextrose | 9.10 | 2.73 |
| Dibutyl Sebacate | 6.14 | 1.85 |
| Titanium Dioxide | 29.71 | 8.91 |
| FD&C Yellow No. 6, HT, 38% | 1.94 | 0.58 |
| D&C Yellow No. 10, HT, 15% | 0.65 | 0.20 |

AQUACOAT is a pseudolatex ethylcellulose dispersion made by FMC Corporation, and DIBUTYL SEBACATE is a plasticizer made by Union Comp.

The standard AQUACOAT formula is prepared as follows:

a) add the HPMC E-5 to 3 times its weight of boiling water;

b) let HPMC solution cool to room temperature and add additional water to obtain a 19% w/w solution;

c) while stirring, add 1.85 grams DIBUTYL SEBACATE to the AQUACOAT solution, and stir together for 30 minutes;

d) blend the titanium dioxide and remaining pigment together;
e) while stirring, add the titanium dioxide and pigment mixture to the 19% w/w HPMC solution;
f) add the AQUACOAT/DIBUTYL SEBACATE mixture to the HPMC solution/titanium dioxide-pigment mixture, and stir for 10 minutes; and
g) add sufficient amount of water to obtain final volume and stir for 10 minutes.

The modified AQUACOAT formula is prepared using the above procedure, except polydextrose is blended with the titanium dioxide and remaining pigment in step (d).

The adhesion value for the modified AQUACOAT formula is 130.40 (±7.94) kPa, whereas the adhesion value for the standard AQUACOAT formula is only 61.65 (±16.23) kPa.

Adhesion in General

Figure 17:
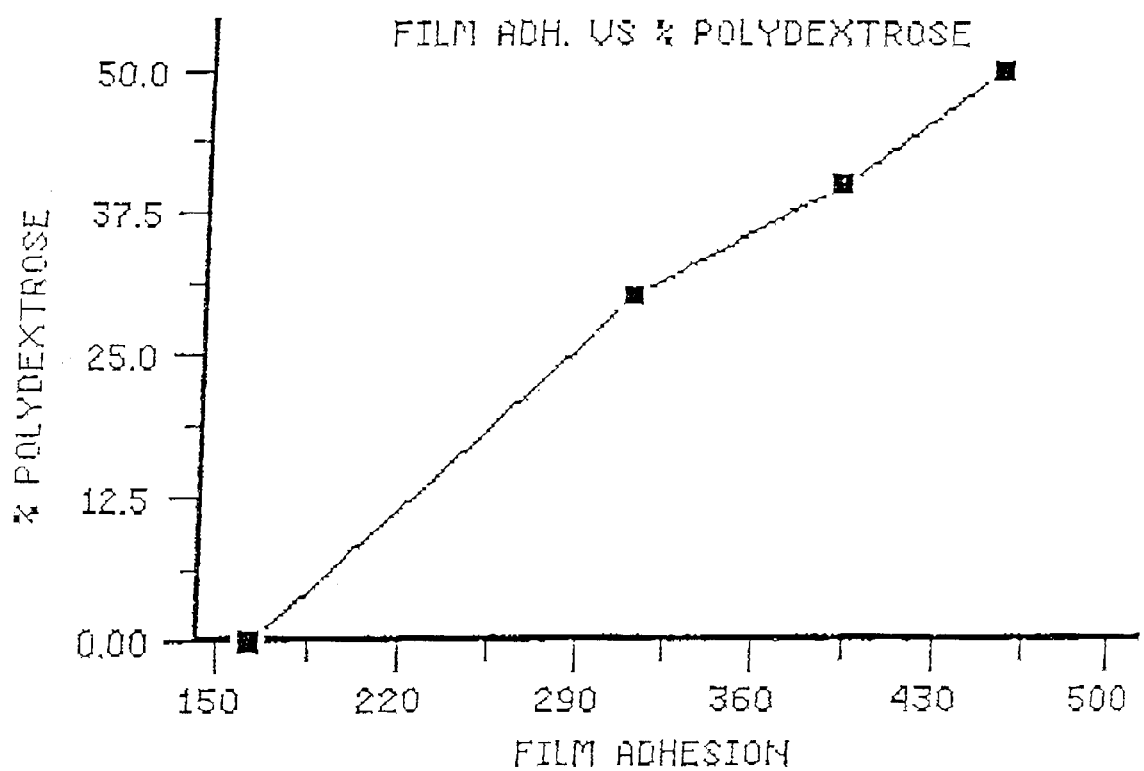
FIG. 17 shows a graph illustrating a film adhesion study of polydextrose.

The addition of polydextrose to standard polymers used in film coating improves the properties of the film coating. For example, the following chart and the graph of FIG. 17 illustrate an improvement in adhesion properties as polydextrose is added HPMC formula.

| Film Adhesion Study of Polydextrose | | |
| --- | --- | --- |
| Run Number | % Polydextrose based on the weight of the total HPMC/polydextrose formula | Film adhesion (kpa) |
| 1 | 0.0 | 163.07 |
| 2 | 30.0 | 310.02 |
| 3 | 40.0 | 390.91 |
| 4 | 50.0 | 452.64 |

For run no. 1, the following formula is used:

| Formula for Run No. 1 | | |
| --- | --- | --- |
| | % | Grams |
| HPMC 6 cps | 69.51 | 139.02 |
| Titanium Dioxide | 11.59 | 23.18 |
| PEG 400 | 6.95 | 13.90 |
| FD&C Yellow No. 6, HT, 18% | 6.65 | 13.30 |
| FD&C Yellow No. 10, HT, 18% | 5.30 | 10.60 |

The mixing procedure for the film coating based on the run no. 1 formula is the same as the mixing procedure set out in Example 15.

Placebos are sprayed at 15% solids and 3% weight gain. During the coating procedure, the inlet air is 60° C., the outlet air is 40° C., the atomizing air is 3 bar, and the feed rate is 10 grams/minute. The charge 995 grams standard placebos and 5 grams flat-faced MCC/STARCH 1500 placebos mentioned in Example 15.

For run no. 2, 21.00 grams of the run no. 1 blended formula is mixed together with 9.00 grams of polydextrose powder, and this mixture is mixed into 170 milliliters of distilled water to make an aqueous coating. The spraying parameters are the same as those for the run no. 1 formula coating.

For run no. 3, 18.00 grams of the run no. 1 blended formula is mixed together with 12.00 grams of polydextrose powder, and this mixture is mixed into 170 milliliters of distilled water to make an aqueous coating. The spraying parameters are the same as those for the run no. 1 formula coating.

For run no. 4, 15.00 grams of the run no. 1 blended formula is mixed together with 15.00 grams of polydextrose powder, and this mixture is mixed into 170 milliliters of distilled water to make an aqueous coating. The spraying parameters are the same as those for the run no. 1 formula coating.

Example 19

A comparison of viscosities is made between the following standard HPMC formula and the following modified HPMC formula having polydextrose:

| Standard HPMC Formula | | |
| --- | --- | --- |
| | % | Grams |
| HPMC 3 cps | 32.66 | 16.33 |
| HPMC 6 cps | 32.66 | 16.33 |
| Titanium Dioxide | 20.67 | 10.34 |
| PEG 400 | 8.01 | 4.00 |
| FD&C Blue No. 1, FG, 3–5% | 6.00 | 3.00 |

| Modified HPMC Formula | | |
| --- | --- | --- |
| | % | Grams |
| Polydextrose | 32.66 | 16.33 |
| HPMC 3 cps | 16.33 | 8.17 |
| HPMC 6 cps | 16.33 | 8.17 |
| Titanium Dioxide | 20.67 | 10.34 |
| PEG 400 | 8.01 | 4.00 |
| FD&C Blue No. 1, FG, 3–5% | 6.00 | 3.00 |

These film coatings are appropriate for coating Amitriptylene tablets, a drug having a somewhat waxy texture that is difficult to coat.

The mixing procedure for each formula is to blend all dry ingredients together for approximately 30 seconds, and add the PEG 400 and blend for an additional 30 seconds.

Dispersions having various percent solids levels are prepared for each formula, and the viscosities of each dispersion is measured in a Brookfield Syncho-Lectric viscometer, (model RV) made by Brookfield Engineering Laboratories, Inc., Stoughton, Mass.

To obtain a 25% solids level, 50 grams of blended formula is dispersed in 150 milliliters distilled water. A 20% solids level is obtained by dispersing 50 grams of blended formula in 200 milliliters distilled water, a 15% solids level is obtained by dispersing 50 grams of blended formula in 283.33 milliliters distilled water, a 10% solids level is obtained by dispersing 50 grams of blended formula in 450 milliliters distilled water, and a 5% solids level is obtained by dispersing 50 grams of blended formula in 950 milliliters distilled water.

Each dispersion is stirred for 30 minutes and then allowed to dearate before being placed in the viscometer. A spindle of the viscometer is lowered into the dispersion to the appropriate depth as marked on the spindle stem, and the viscometer is turned on. After a few rotations of the spindle, a reading of the viscosity of the dispersion is obtained, and is converted into centipoise using a Brookfield factor finder. For the 15% dispersion, spindle no. 2 of the viscometer is used and the dispersions are tested at 4, 10 and 20 rotations of the spindle per minute to obtain an average viscosity reading.

Figure 18:
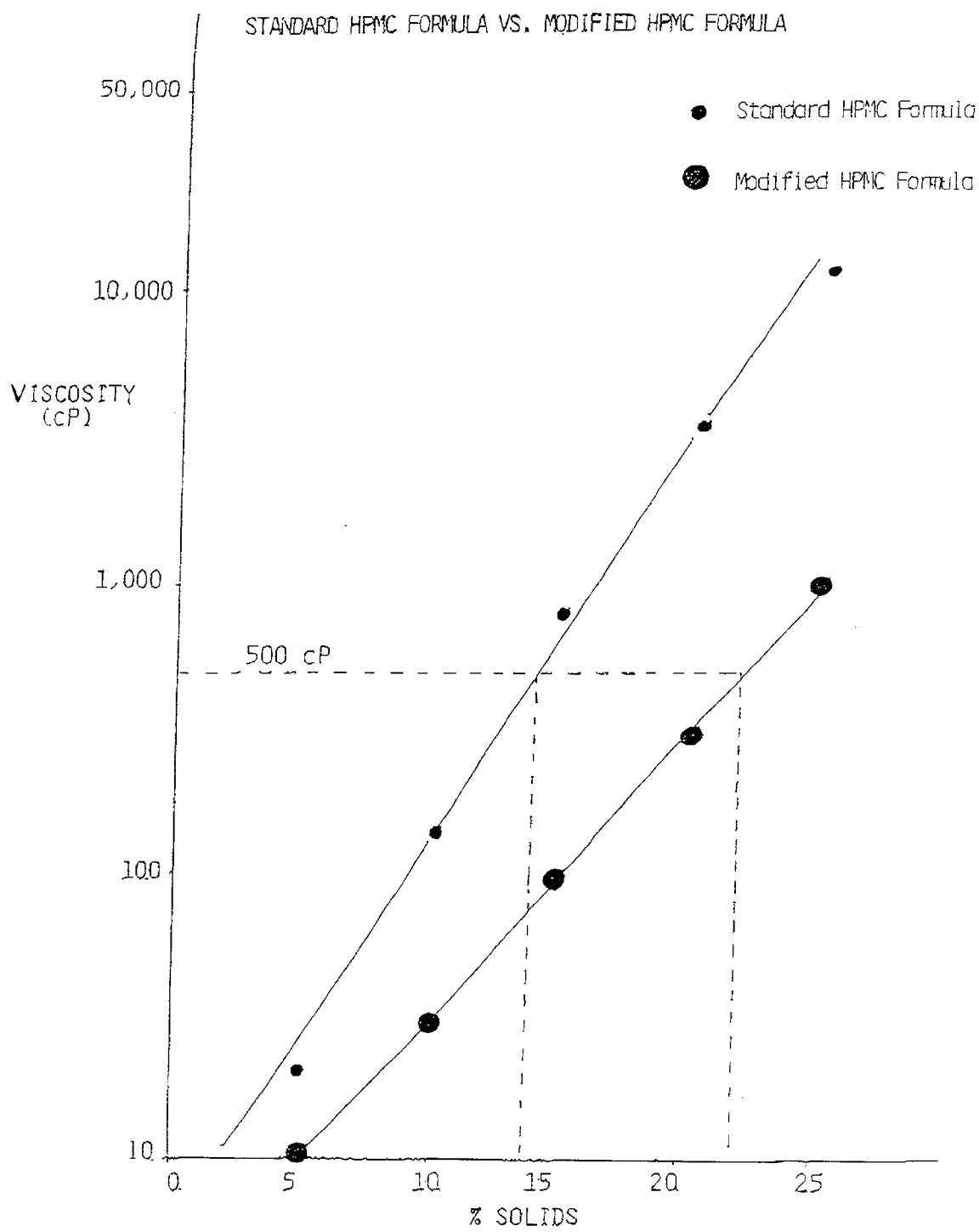
FIG. 18 shows a graph illustrating the results of Example 19.

The results are illustrated in the following chart and the graph of FIG. 18. As is seen from the chart and the graph of FIG. 18, at each solids percentage, the modified HPMC formula having polydextrose has a considerably lower viscosity than the standard HPMC formula.

VISCOSITY COMPARISONS

| % Solids | Standard HPMC Formula (cP) | "Modified" Formula (cP) |
|---|---|---|
| 25 | 2875 | 544 |
| 20 | 898 | 224 |
| 15 | 275 | 54 |
| 10 | 64 | 20 |
| 5 | 16 | 10 |

Example 20

An aqueous film coating is prepared having a 15% solids level by dispersing 50 grams of the following standard HPMC formula into 283.33 grams distilled water, and the measured viscosity of the aqueous film coating is 673 centipoise (cP).

Standard HPMC Formula

|  | % | Grams |
|---|---|---|
| HPMC (6 cps) | 69.51 | 34.75 |
| Titanium Dioxide | 11.59 | 5.79 |
| PEG 400 | 6.95 | 3.48 |
| FD&C Yellow No. 6, HT, 18% | 6.65 | 3.33 |
| D&C Yellow No. 10, HT, 17% | 5.30 | 2.65 |

A second aqueous film coating is prepared using the following modified HPMC formula having polydextrose, and its solids are increased until its viscosity substantially matches the viscosity of the standard HPMC formula film coating. At this equivalent viscosity, the modified HPMC formula film coating has a 23% solids level (50 grams of modified formula dispersed into 167.39 grams distilled water).

Modified HPMC Formula

|  | % | Grams |
|---|---|---|
| HPMC (6 cps) | 34.755 | 17.385 |
| Polydextrose | 34.755 | 17.385 |
| Titanium Dioxide | 11.59 | 5.79 |
| PEG 400 | 6.95 | 3.48 |
| FD&C Yellow No. 6, HT, 18% | 6.65 | 3.33 |
| D&C Yellow No. 10, HT, 17% | 5.30 | 2.65 |

Example 21

An aqueous film coating is prepared having a 15% solids level by dispersing 300 grams of the following standard HPMC formula into 1700 milliliters distilled water:

Standard HPMC Formula

|  | % | Grams |
|---|---|---|
| HPMC (6 cps) | 69.51 | 208.53 |
| Titanium Dioxide | 11.59 | 34.77 |
| PEG 400 | 6.95 | 20.85 |
| FD&C Yellow No. 6, HT, 18% | 6.65 | 19.95 |
| D&C Yellow No. 10, HT, 17% | 5.30 | 15.90 |

A second aqueous film coating is prepared by dispersing 300 grams of the following modified HPMC formula having polydextrose into 1700 milliliters of distilled water.

Modified HPMC Formula

|  | % | Grams |
|---|---|---|
| HPMC (6 cps) | 34.755 | 104.265 |
| Polydextrose | 34.755 | 104.265 |
| TiO2 | 11.59 | 34.77 |
| PEG 400 | 6.95 | 20.85 |
| FD&C Yellow No. 6, HT, 18% | 6.65 | 19.95 |
| D&C Yellow No. 10, HT, 17% | 5.30 | 15.90 |

Using a 24 inch Accela Cota coating pan, the standard HPMC formula film coating is sprayed onto a first set of waxy tablets (oval placebos), and the modified HPMC formula film coating is sprayed onto a second set of waxy tablets (oval placebos). The spray coating parameters are shown in the following chart.

ACCELA-COTA COMPARISONS OF STANDARD HYDROXYPROPYL METHYLCELLULOSE (HPMC) FORMULA VS. MODIFIED HPMC FORMLA AT EQUIVALENT VISCOSITIES

|  | Standard Formulation | Modified Formulation |
|---|---|---|
| VISCOSITY (centipoise) | 673 cps | 597 cps |
| % SOLIDS | 15% | 23% |
| WEIGHT GAIN OF COATED TABLETS | 3% | 3% |
| CHARGE (kilograms) | 10 kgs | 10 kgs |
| FLOW RATE | 75 grams/min. | 95 grams/min |
| INLET TEMP (° C.) | 80° C. | 80° C. |
| OUTLET TEMP (° C.) | 40° C. | 40° C. |
| ATOMIZING AIR (psi) | 45 psi | 45 psi |
| PAN RPM | 12 rpm | 12 rpm |
| COATING TIME (min.) | 30 min. | 14 min. |

The flow rate is faster for the modified HPMC formula film coating than it is for the standard HPMC formula film coating because the modified HPMC formula film coating is easier to pump than the standard HPMC formula film coating and because the modified HPMC formula film coating atomizes better than the standard HPMC formula film coating.

As shown in the above chart, with the inclusion of polydextrose in the modified HPMC formula film coating, the spraying time is one half the spraying time of the standard HPMC formula film coating. Further, as is shown FIGS, 1 and 2, the reduced spraying time of the modified HPMC formula film coating does not adversely affect coating of the logo on the placebo (i.e., no bridging). The modified HPMC formula film coating at a 23% solids level looks as good as the standard HPMC formula film coating at a 15% solids level.

Using the modified HPMC formula film coating with its higher percentage solids level, spraying time is effectively reduced without adversely affecting coating of the logo on the placebos.

Example 22

A light stability comparison is made between the film coatings having the following formulas. These coatings are typically used on an ibuprofen substrate.

| Standard HPMC Formula (Orange Color) | | |
|---|---|---|
| | % | Grams |
| HPMC 6 cps | 72.09 | 18.02 |
| Titanium Dioxide | 12.00 | 3.00 |
| PEG 400 | 10.00 | 2.50 |
| FD&C Yellow No. 6, HT, 40% | 2.25 | 0.56 |
| FD&C Yellow No. 6, HT, 17% | 3.66 | 0.92 |

| Modified HPMC Formula (Orange Color) | | |
|---|---|---|
| | % | Grams |
| Polydextrose | 33.70 | 8.42 |
| HPMC 6 cps | 26.96 | 6.74 |
| HPMC 50 cps | 6.74 | 1.69 |
| Titanium Dioxide | 12.09 | 3.02 |
| PEG 8000 | 6.10 | 1.53 |
| Sodium Alginate (Kelgin LV) | 4.10 | 1.02 |
| Alcolec F-100 | 2.40 | 0.60 |
| Triacetin | 2.00 | 0.50 |
| FD&C Yellow No. 6, HT, 40% | 2.25 | 0.56 |
| FD&C Yellow No. 6, HT, 17% | 3.66 | 0.92 |

In addition to the polydextrose added to the modified formula, it is desirable to add sodium alginate (KELGIN LV) and ALCOLEC F-100 to the modified formula when coating a difficult-to-coat/waxy substrate such as potassium chloride tablets and large dosage tablets such as ibuprofen tablets and caltrate tablets. Also, since the presence of sodium alginate in the formula tends to slightly increase the viscosity of the formula, the formulae is limited to a 15% solids level.

To analyze color, a card method is used. Under the card method, a drawdown card is made, placed in a fadeometer for eight hours and analyzed during this time on a reflectance spectrophotometer.

The drawdown card is made as follows:
(a) equipment:
reflectance spectrophotometer (Spectro-Sensor II); Applied Color Systems, Princeton, N.J.
Bird applicator, 0.006 inch; Gardner/Neotec Instrumentation, Silver Spring, Md.
all white WDX-2 4"×5" form (white cardboard card); Lenetra Corporation, Ho-Ho-Kus, N.J.
Bird vacuum plate; Gardner/Neotec Instrumentation, Silver Spring, Md.
(b) procedure:
1. Add 25 grams of formula to 75 milliliters boiling water in a 250 milliliter beaker while mixing at a moderate speed with a Jiffy mixer.
2. Mix for approximately one minute.
3. Place the dispersion in an icebath for 30 minutes.
4. Remove air bubbles from the dispersion with a vacuum desiccator. This takes approximately 20–30 minutes, but is formula dependent.
5. Using a 0.006 Bird applicator, apply a uniform film of the dispersion to a 4"×5" white cardboard card. (Hold the card motionless using the vacuum plate.)
6. Allow the card to dry away from light at room temperature or place in an oven (preferably a forced air oven) at 45° C. for 5–10 minutes.
7. Analyze card on reflectance spectrophotometer and compare to a standard (i.e., standard formula versus modified formula).

For formulas containing sodium alginate and Alcolec F-100, the following procedure is used:
1. Add 25 grams of formula to 75 milliliters (ml.) of boiling water in a 250 ml. beaker while mixing at a moderate speed with a Jiffy mixer, and add 25 grams of 15% aqueous polymer solution having the following formula:

| Ingredients | % By Weight | Grams |
|---|---|---|
| HPMC E-15 | 13.50 | 3.370 |
| PEG 3350 | 1.50 | .375 |
| distilled water | 85.00 | 21.250 |

Follow steps 2–7 in above procedure.

Figure 19:
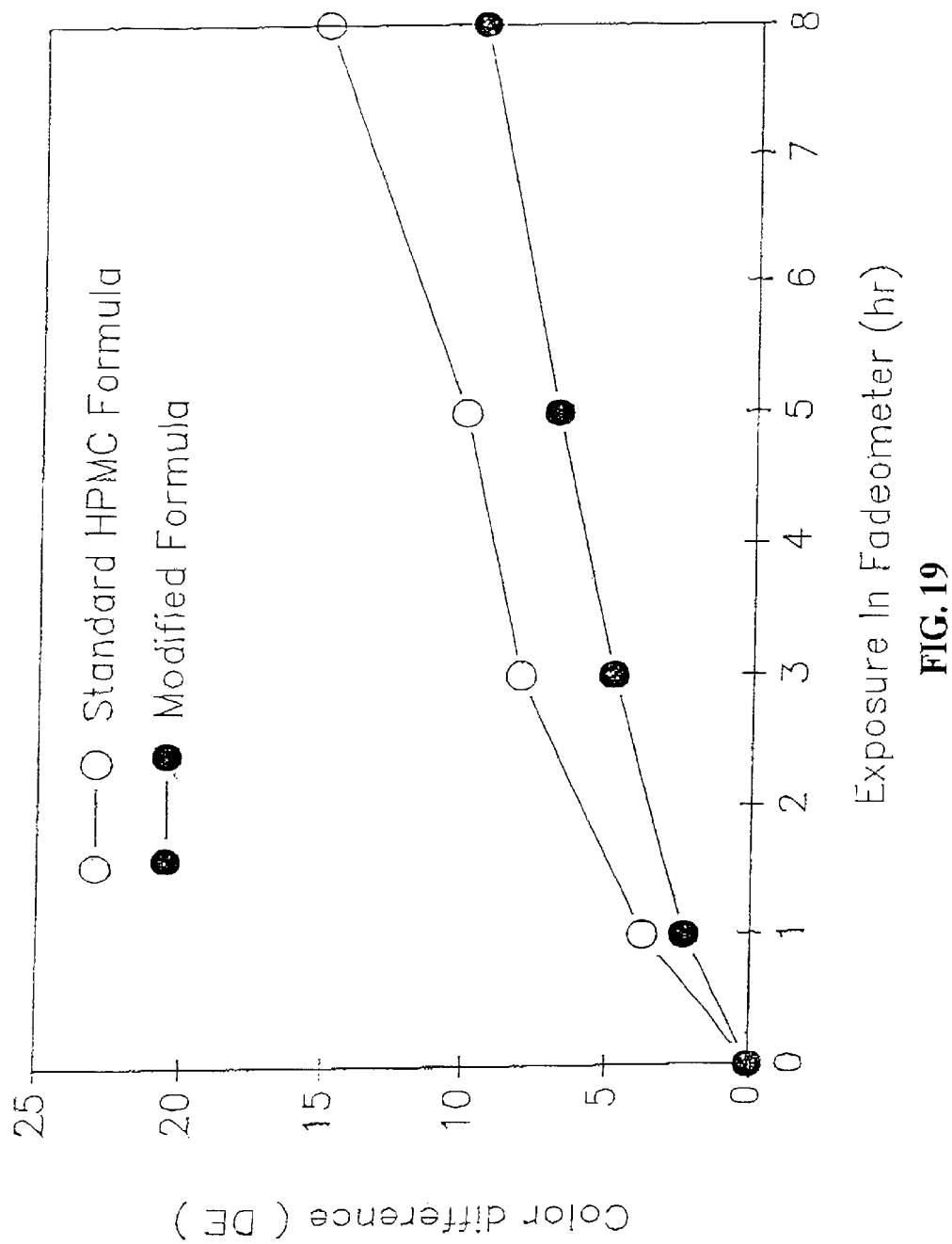
FIG. 19 shows a graph illustrating the results of Example 22.

The results of the analysis of color difference (labeled as "DE" or "ΔE") for each film coating are shown in the following chart and the graph of FIG. 19. Low DE values signify better light stability of the film coating.

As the results show, the color difference for the modified HPMC formula film coating having polydextrose is lower than the color difference for the standard HPMC formula film coating, thereby indicating that the modified HPMC formula film coating having polydextrose has greater color stability in accelerated light conditions than the standard HPMC formula film coating.

| | COLOR DIFFERENCE COMPARISONS | |
|---|---|---|
| Hours | DE Values For Standard HPMC Formula-Orange Color | DE Values For Modified HPMC Formula-Orange Color |
| 1 | 3.76 | 2.33 |
| 3 | 8.08 | 4.88 |
| 5 | 10.12 | 6.88 |
| 8 | 15.19 | 9.58 |

A discussion of color analysis is presented by Stuart C. Porter and Kathleen Saraceni in "Opportunities for Cost Containment in Aqueous Film Coating", Pharmaceutical Technology (September 1988), incorporated herein by reference.

Example 23

A light stability comparison is made between the film coatings having the following formulas using the procedures of Example 22. These coatings are typically used on DEX-ATRIM tablets.

| Standard Hydroxypropyl Methylcellulose (HPMC)/ Hydroxypropyl Cellulose (HPC) Formula--Yellow Color | | |
| --- | --- | --- |
| | % | Grams |
| HPMC 3 cps | 35.00 | 8.75 |
| Klucel EF | 30.00 | 7.50 |
| titanium dioxide | 16.30 | 4.07 |
| PEG 400 | 10.00 | 2.50 |
| HPMC 50 cps | 5.00 | 1.25 |
| D&C yellow No. 10, HT, 17% | 3.51 | 0.88 |
| FD&C yellow No. 6, HT, 17% | 0.19 | 0.05 |

| Modified HPMC/Polydextrose Formula--Yellow Color | | |
| --- | --- | --- |
| | % | Grams |
| polydextrose | 35.00 | 8.75 |
| HPMC 3 cps | 17.50 | 4.37 |
| HPMC 6 cps | 15.00 | 3.75 |
| titanium dioxide | 16.30 | 4.07 |
| PEG 400 | 10.00 | 2.50 |
| HPMC 50 cps | 2.50 | 0.63 |
| D&C Yellow No. 10, HT, 17% | 3.51 | 0.88 |
| FD&C Yellow No. 6, HT, 17% | 0.19 | 0.05 |

Figure 20:
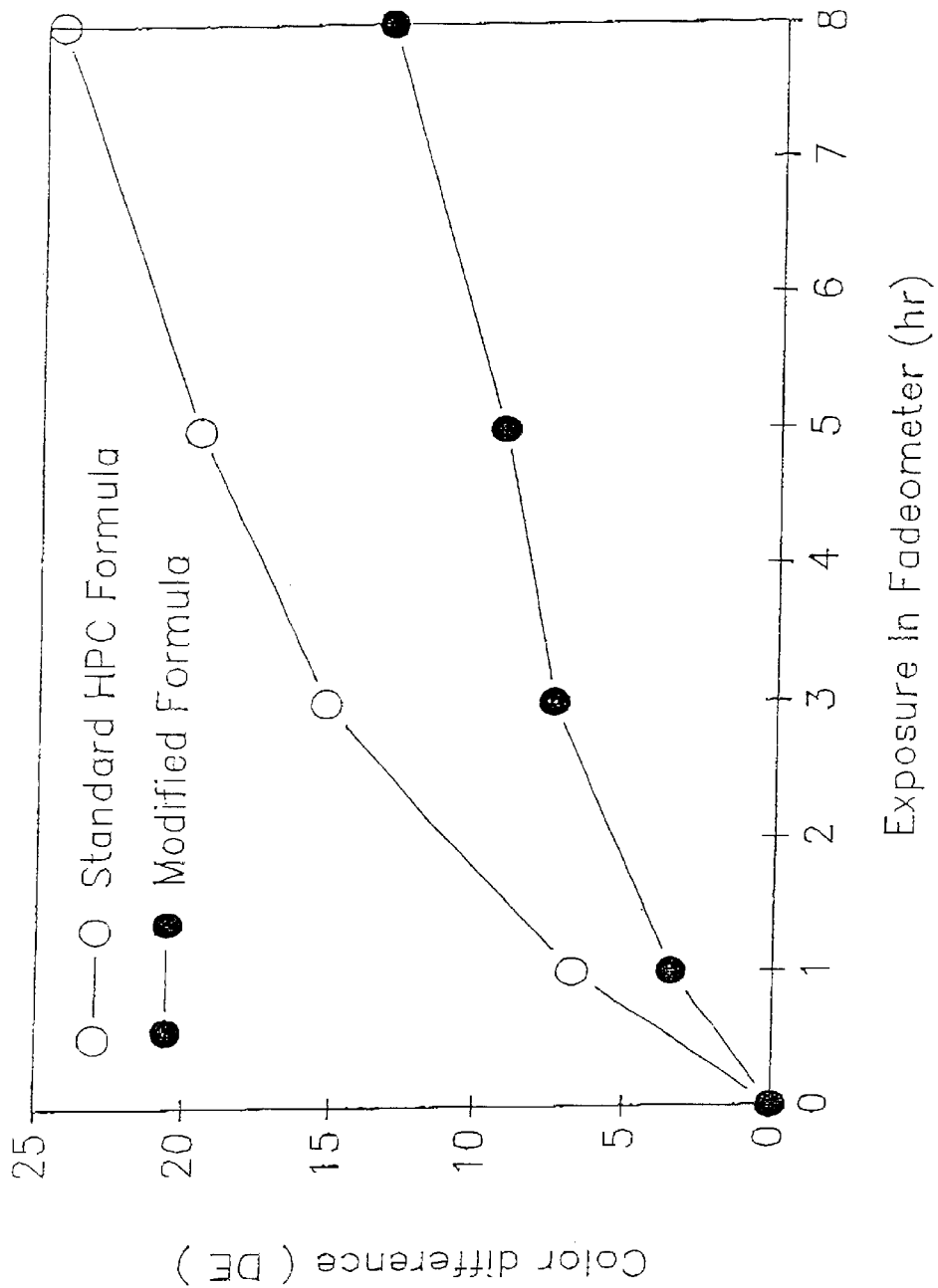
FIG. 20 shows a graph illustrating the results of Example 23.

The results shown in the following chart and the graph of FIG. 20 show that the modified HPMC/Polydextrose formula film coating having polydextrose has better color stability in accelerated light conditions than the standard HPMC/HPC formula film coating.

| Color Difference Comparisons | | |
| --- | --- | --- |
| Hours | DE Values For Standard HPMC/HPC Formula-Yellow Color | DE Values For Modified HPMC/Polydextrose Formula-Yellow Color |
| 1 | 6.73 | 3.45 |
| 3 | 15.31 | 7.47 |
| 5 | 19.71 | 9.24 |
| 8 | 24.45 | 13.28 |

Example 24

A light stability comparison is made between film coatings having the following formulas using the procedures of Example 22. These coatings are typically used on DIMETAPP tablets.

| Standard HPMC Formula--Blue Color | | |
| --- | --- | --- |
| | % | Grams |
| HPMC 3 cps | 33.50 | 8.38 |
| HPMC 6 cps | 33.50 | 8.38 |
| titanium dioxide | 23.12 | 5.77 |
| PEG 800 | 8.00 | 2.00 |
| FD&C Blue No. 1, FG, 4% | 1.88 | 0.47 |

| Modified HPMC Formula--Blue Color | | |
| --- | --- | --- |
| | % | Grams |
| polydextrose | 33.50 | 8.38 |
| HPMC 3 cps | 16.75 | 4.19 |
| HPMC 6 cps | 16.75 | 4.19 |
| titanium dioxide | 23.12 | 5.77 |
| PEG 400 | 8.00 | 2.00 |
| FD&C Blue No. 1, FG, 4% | 1.88 | 0.47 |

Figure 21:
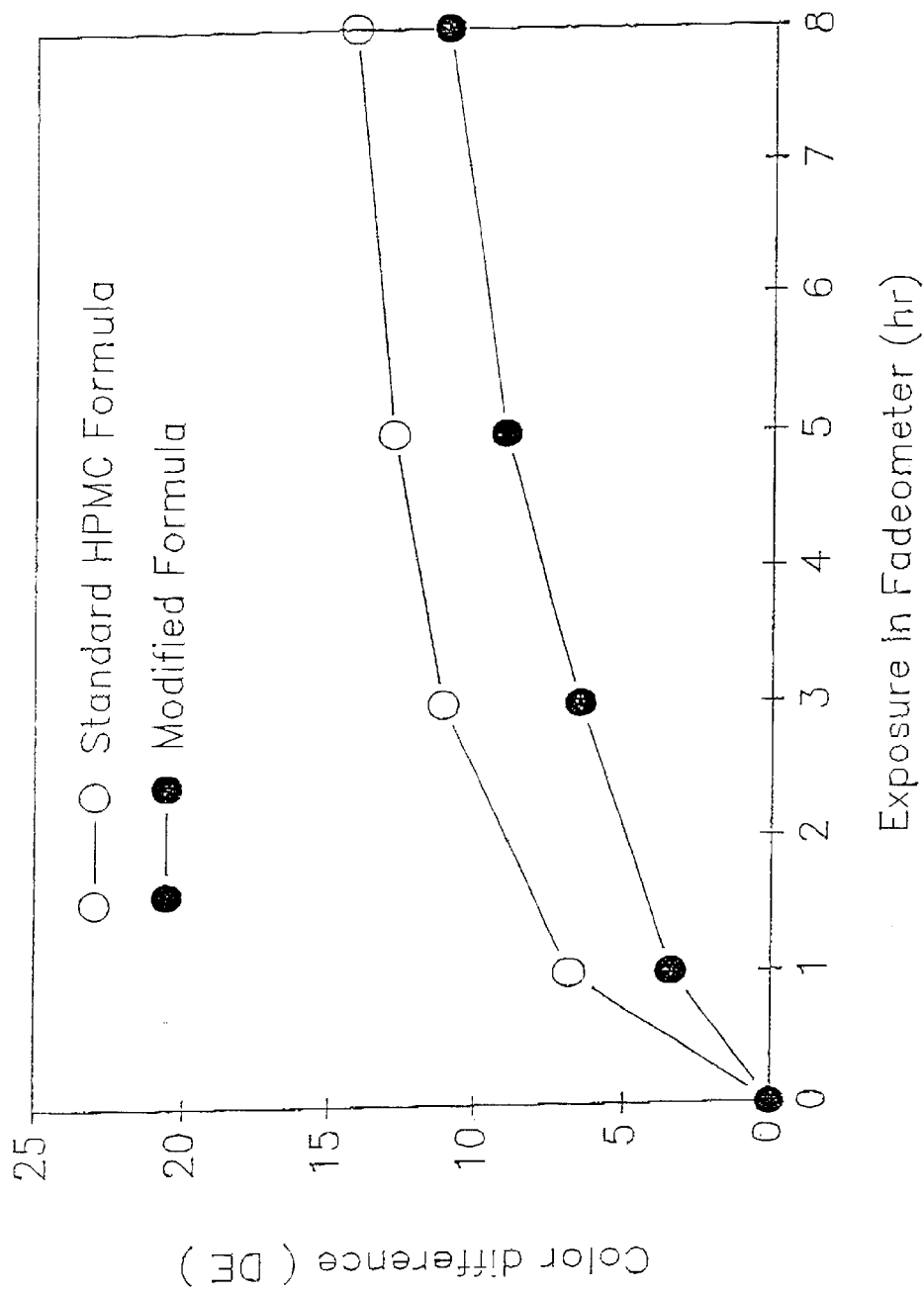
FIG. 21 shows a graph illustrating the results of Example 24.

The results of the comparison are shown in the following chart and the graph of FIG. 21.

| Color Difference Comparisons | | |
| --- | --- | --- |
| Hours | DE Values For Standard HPMC Formula-Blue Color | DE Values For Modified HPMC Formula-Blue Color |
| 1 | 6.29 | 3.42 |
| 3 | 11.13 | 6.49 |
| 5 | 12.85 | 9.05 |
| 8 | 14.20 | 11.02 |

Again, the results show that the addition of polydextrose to an HPMC film coating leads to better color stability of the film coating in accelerated light conditions.

Example 25

A light stability comparison is made between film coatings having the following formulas. These coatings are typically used on oyster shell tablets.

| HPMC/HPC Formula--Grey Color | | |
| --- | --- | --- |
| | % | Grams |
| HPMC 6 cps | 35.00 | 8.75 |
| Klucel EF | 30.00 | 7.50 |
| HPMC 50 cps | 5.00 | 1.25 |
| titanium dioxide | 19.30 | 4.82 |
| PEG 400 | 10.00 | 2.50 |
| FD&C Yellow No. 6, HT, 18% | 0.34 | 0.09 |
| FD&C Blue No. 2, HT, 12% | 0.28 | 0.07 |
| FD&C Red No. 40, HT, 17% | 0.08 | 0.02 |

| HPMC/Polydextrose Formula--Grey Color | | |
| --- | --- | --- |
| | % | Grams |
| polydextrose | 32.70 | 8.18 |
| HPMC 6 cps | 32.70 | 8.18 |
| titanium dioxide | 19.30 | 4.82 |
| PEG 8000 | 6.10 | 1.52 |
| sodium alginate (Kelgin LV) | 4.10 | 1.02 |
| Alcolec F-100 | 2.40 | 0.60 |
| Triacetin | 2.00 | 0.50 |
| FD&C Yellow No. 6, HT, 18% | 0.34 | 0.09 |
| FD&C Blue No. 2, HT, 12 | 0.28 | 0.07 |
| FD&C Red No. 40, HT, 17 | 0.08 | 0.02 |

Figure 22:
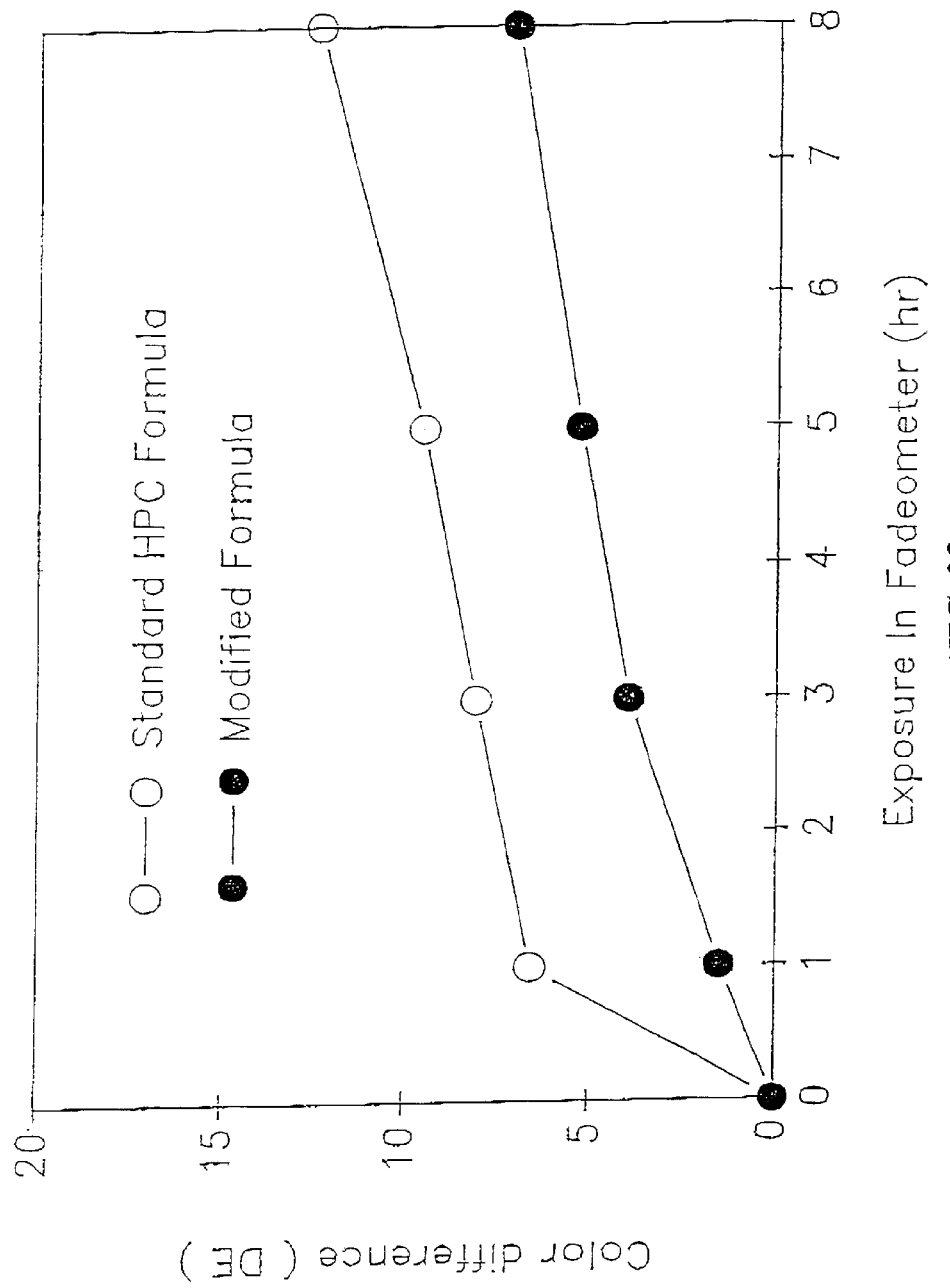
FIG. 22 shows a graph illustrating the results of Example 25.

The results of the comparison are shown in the following chart and the graph of FIG. 22.

| | Color Difference Comparisons | |
|---|---|---|
| Hours | DE Values For HPMC/HPC Formula-Grey Color | DE Values For HPMC/Polydextrose Formula-Grey Color |
| 1 | 6.53 | 1.52 |
| 3 | 8.04 | 4.00 |
| 5 | 9.50 | 5.29 |
| 8 | 12.44 | 7.02 |

The HPMC/Polydextrose formula film coating has a better light stability (lower DE values) than the HPMC/HPC formula film coating.

Example 26

A light stability comparison is made between a film coating having the following standard AQUACOAT formula and a film coating having the following modified AQUACOAT formula having polydextrose:

| Standard AQUACOAT Formula | | |
|---|---|---|
| | % | Grams |
| AQUACOAT ECD-30 (30% w/w) | 30.78 | 9.23 (dry solids) (30.77 grams as a solution) |
| HPMC E-5 (19% w/w) | 30.78 | 9.23 (dry solids) (48.60 grams as a solution) |
| Dibutyl Sebacate | 6.14 | 1.85 |
| Titanium Dioxide | 29.71 | 8.91 |
| FD&C Yellow No. 6, HT, 38% | 1.94 | 0.58 |
| D&C Yellow No. 10, HT, 15% | 0.65 | 0.20 |

| Modified AQUACOAT Formula | | |
|---|---|---|
| | % | Grams |
| polydextrose | 9.10 | 2.73 |
| AQUACOAT ECD-30 (30% w/w) | 26.23 | 7.87 (dry solids) (26.22 grams as a solution) |
| HPMC E-50 (19% w/w) | 26.23 | 7.87 (dry solids) (41.42 grams as a solution) |
| titanium dioxide | 29.71 | 8.91 |
| DIBUTYL SEBACATE | 6.14 | 1.85 |
| FD&C Yellow No. 6, HT, 38 | 1.94 | 0.58 |
| D&C Yellow No. 10, HT, 15% | 0.65 | 0.20 |

The film coatings are prepared and are sprayed onto ⅜ inch round placebos using the procedure set out in Example 18.

To analyze color, a tablet method is used since an adequate film on a card is difficult to obtain with these film coatings. Under the tablet method, ⅜ inch round placebos are sprayed with a film coating having a 15% solids level (3% weight gain to the tablet). The coated tablets are placed in a fadeometer for eight hours and analyzed during this time on a reflectance spectrophotometer.

The equipment used is COLOR FADE-OMETER fade-ometer (Type FDA-R) made by Atlas Electric Devices Co., Chicago, Ill. and a SPECTO-SENSOR II reflectance spectrophotometer made by Applied Color Systems, Princeton, N.J.

Figure 23:
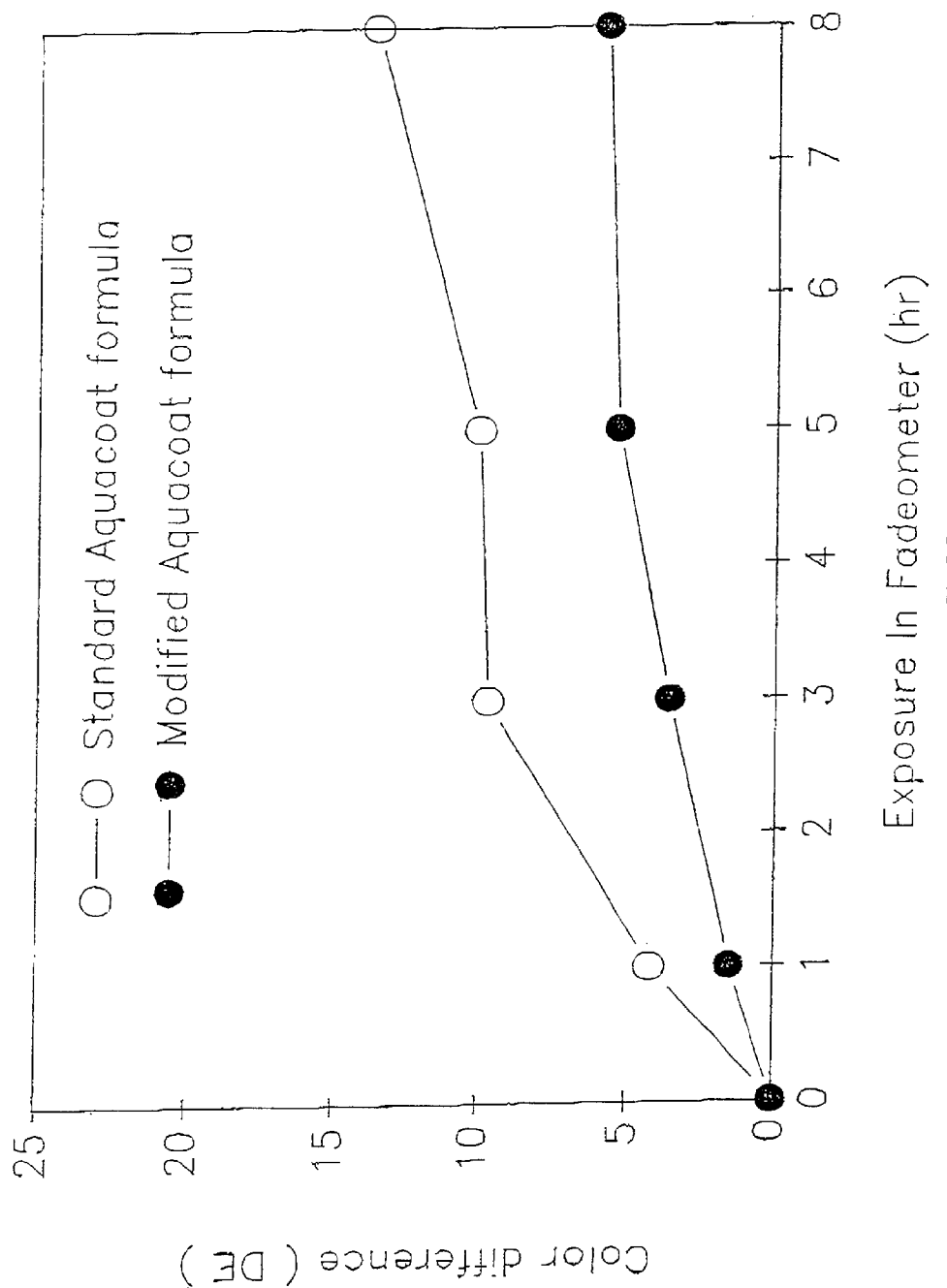
FIG. 23 shows a graph illustrating the results of Example 26.

The results of the comparison are shown in the following chart and the graph of FIG. 23. The modified AQUACOAT formula film coating having polydextrose has a better color stability in accelerated light conditions (lower DE values) than the standard AQUACOAT formula film coating.

| | Color Difference Comparisons | |
|---|---|---|
| Hours | DE Values For Standard AQUACOAT Formula | DE Values For Modified AQUACOAT Formula |
| 1 | 4.24 | 1.53 |
| 3 | 9.73 | 3.61 |
| 5 | 10.06 | 5.39 |
| 8 | 13.71 | 5.85 |

Example 27

Using the procedures of Example 26, light stability comparison is made between a film coating having the following standard EUDRAGIT formula and a film coating having the following modified EUDRAGIT formula having polydextrose:

| Standard EUDRAGIT Formula | | |
|---|---|---|
| | % | Grams |
| EUDRAGIT NE 30 D (30% w/w) | 7.20 | 2.16 (dry solids) (7.2 grams as a solution) |
| PEG 8000 (30% w/w) | 7.20 | 2.16 (dry solids) (7.2 grams as a solution) |
| HPMC E-5 (10% w/w) | 7.20 | 2.16 (dry solids) (21.6 grams as a solution) |
| talc | 43.24 | 12.97 |
| magnesium stearate | 2.40 | 0.72 |
| antifoam agent (AEROSOL OT, 75%) | 0.47 | 0.14 |
| titanium dioxide | 29.70 | 8.91 |
| FD&C Yellow No. 6, HT, 38% | 1.94 | 0.59 |
| D&C Yellow No. 10, HT, 15% | 0.65 | 0.19 |

| Modified EUDRAGIT Formula | | |
|---|---|---|
| | % | Grams |
| polydextrose | 23.08 | 6.92 |
| EUDRAGIT NE 30 D (30% w/w) | 7.20 | 2.16 (dry solids) (7.2 grams as a solution) |
| PEG 8000 (30% w/w) | 7.20 | 2.16 (dry solids) (7.2 grams as a solution) |
| HPMC E-5 (10% w/w) | 7.20 | 2.16 (dry solids) (21.6 grams as a solution) |
| talc | 20.16 | 6.05 |
| magnesium stearate | 2.40 | 0.72 |
| antifoam agent (AEROSOL OT, 75%) | 0.47 | 0.14 |
| titanium dioxide | 29.70 | 8.91 |
| FD&C Yellow No. 6, HT, 38% | 1.94 | 0.59 |
| D&C Yellow No. 10, HT, 15% | 0.65 | 0.19 |

EUDRAGIT NE 30 D is an aqueous acrylic latex coating dispersion made by Rohm Pharma, and AEROSOL OT is an anti-foaming agent made by American Cyanamid.

The standard EUDRAGIT formula is prepared as follows:

a) while continuously stirring, add HPMC E-5 to 3 times its weight of boiling water;
b) let HPMC solution cool to room temperature and add additional water to obtain a 10% w/w solution;
c) while stirring, sequentially add the talc, magnesium stearate, antifoam agent, and 10% w/w HPMC solution to 148.48 grams distilled water;
d) prepare a 30% PEG 8000 solution by dissolving 30 grams PEG 8000 into 70 grams distilled water;
e) add 7.20 grams of the 30% PEG 8000 solution to the mixture formed in step (c);
f) disperse titanium dioxide and remaining pigment together in a blender jar, and add this titanium dioxide/pigment to the mixture formed in step (e);
g) just prior to use, while slowly stirring, add 7.2 grams 30% w/w solution of EUDRAGIT to mixture formed in step (f).

The modified EUDRAGIT formula is prepared using the above procedure, except polydextrose is blended with the titanium dioxide and remaining pigment in step (f).

The spraying procedure for each coating is set out in Example 15.

Figure 24:
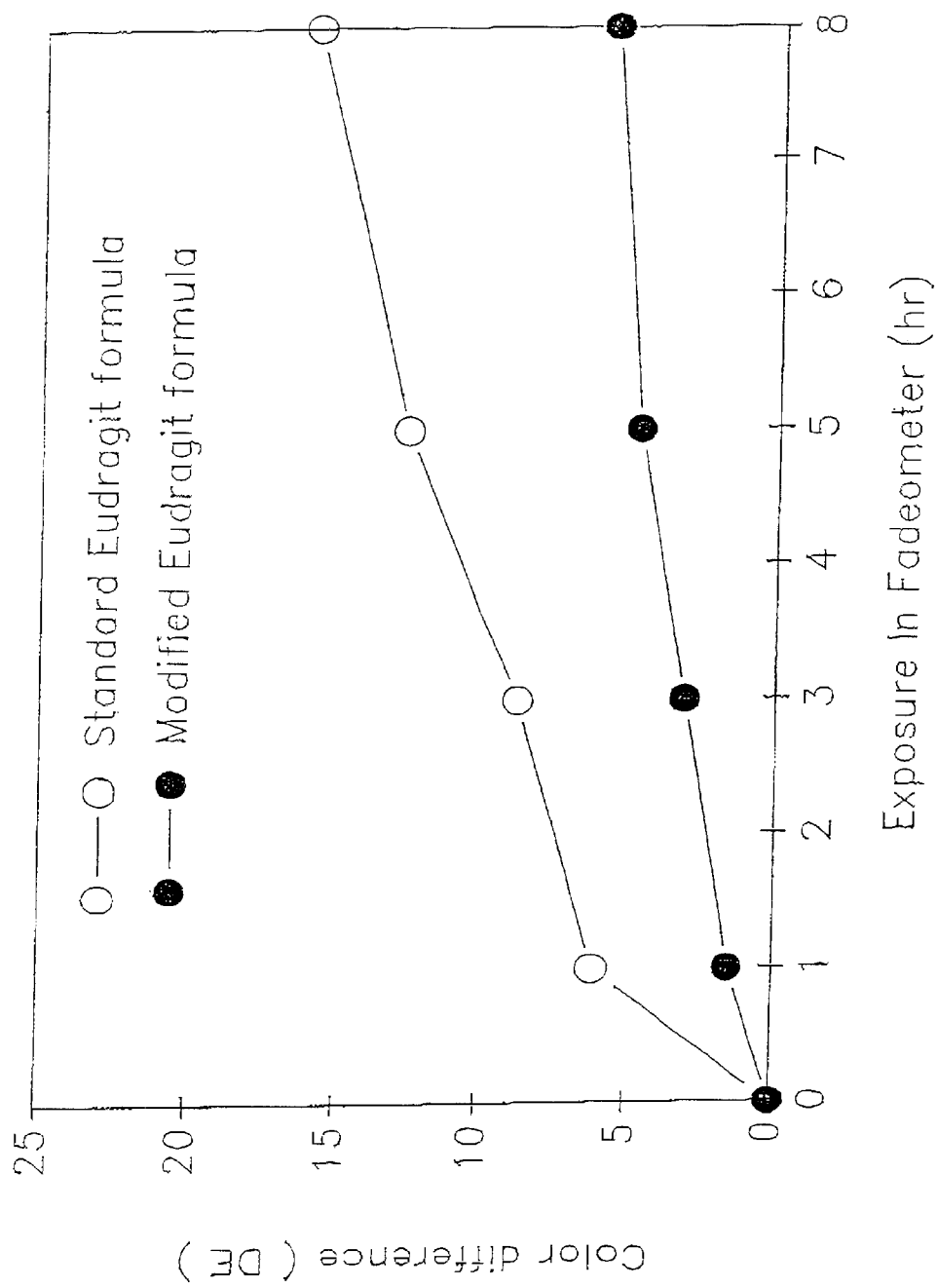
FIG. 24 shows a graph illustrating the results of Example 27.

The results shown in the following chart and the graph of FIG. 24 show that the modified EUDRAGIT formula film coating having polydextrose has a better color stability in accelerated light conditions (lower DE values) than the standard EUDRAGIT formula film coating.

| | Color Difference Comparisons | |
|---|---|---|
| Hours | DE Values For Standard EUDRAGIT Formula | DE Values For Modified EUDRAGIT Formula |
| 1 | 6.08 | 1.52 |
| 3 | 8.75 | 3.10 |
| 5 | 12.65 | 4.71 |
| 8 | 15.90 | 5.68 |

Example 28

Using the procedures of Example 26, a light stability comparison is made between a film coating having the following standard water-soluble cellulose acetate film coating formula and a film coating having the following modified water-soluble cellulose acetate formula having polydextrose:

| Standard Water-Soluble Cellulose Acetate Formula | | |
|---|---|---|
| | % | Grams |
| medium viscosity cellulose acetate | 60.70 | 18.21 |
| titanium dioxide | 29.71 | 8.91 |
| glycerine | 7.00 | 2.10 |
| FD&C Yellow No. 6, HT, 38% | 1.94 | 0.58 |
| FD&C Yellow No. 10, HT, 15% | 0.65 | 0.20 |

| Modified Water-Soluble Cellulose Acetate Formula | | |
|---|---|---|
| | % | Grams |
| polydextrose | 23.08 | 6.92 |
| medium viscosity cellulose acetate | 37.62 | 11.28 |
| titanium dioxide | 29.71 | 8.91 |
| glycerine | 7.00 | 2.10 |
| FD&C Yellow No. 6, HT, 38% | 1.94 | 0.58 |
| FD&C Yellow No. 10, HT, 15% | 0.65 | 0.20 |

The water-soluble cellulose acetate is made by Celanese, and the glycerine is used as a plasticizer and is made by Dow Chemical Company.

The film coatings are prepared an sprayed using the procedures set out in Example 15.

Figure 25:
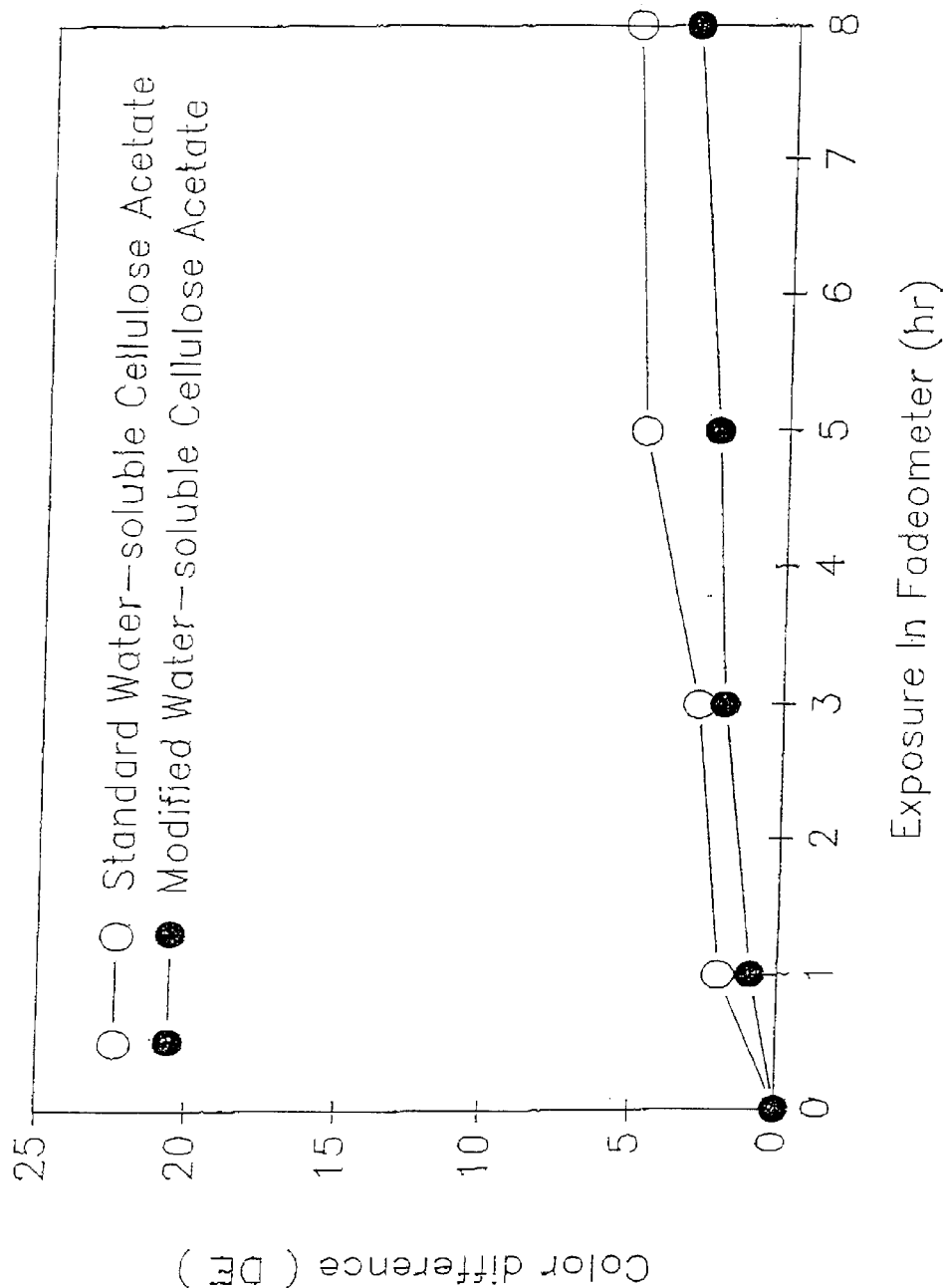
FIG. 25 shows a graph illustrating the results of Example 28.

The results shown in the following chart and the graph of FIG. 25 show that the modified water-soluble cellulose acetate formula film coating having polydextrose has a better color stability in accelerated light conditions (lower DE values) than the standard water-soluble cellulose acetate formula film coating.

| | Color Difference Comparisons | |
|---|---|---|
| Hours | DE Values For Standard Water-Soluble Cellulose Acetate Formula | DE Values for Modified Water-Soluble Cellulose Acetate Formula |
| 1 | 2.04 | 0.95 |
| 3 | 2.89 | 2.01 |
| 5 | 4.90 | 2.40 |
| 8 | 5.41 | 3.57 |

Example 29

Figure 3:
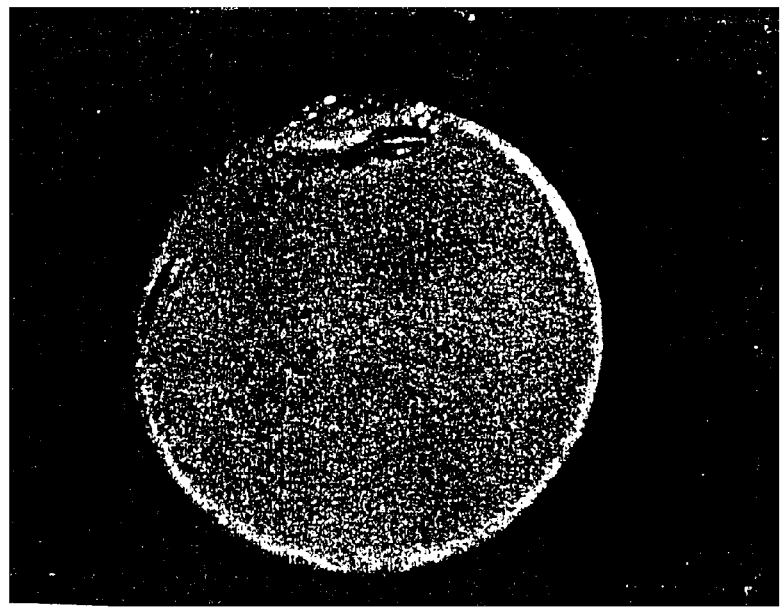
FIG. 3 shows photomicrograph A illustrating an HPMC formula film coating.

A film coating based on the following HPMC formula is sprayed on hydrophobic tablet substrates, and one such coated tablet is shown in photomicrograph A of FIG. 3. The mixing and spraying procedures for this coating are the same as those in Example 16.

| HYDROXYPROPYL METHYLCELLULOSE FORMULATION | | |
|---|---|---|
| | % | Grams |
| HPMC E-5 | 61.36 | 18.40 |
| Titanium Dioxide | 29.70 | 8.91 |
| PEG 400 | 6.35 | 1.91 |
| FD&C Yellow No. 6, HT, 39% | 1.94 | 0.58 |
| D&C Yellow No. 10, HT, 17% | 0.65 | 0.20 |

Figure 4:
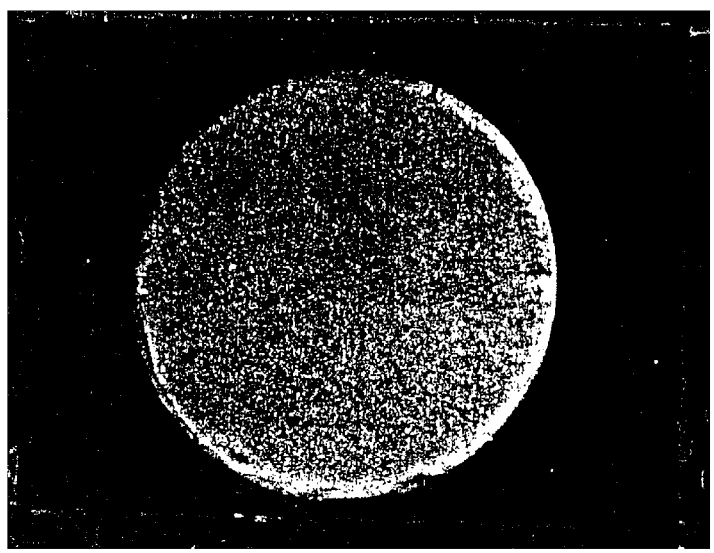
FIG. 4 shows photomicrograph B illustrating an HPMC/polydextrose formula film coating.

A film coating based on the following HPMC/Polydextrose formula also is sprayed on hydrophobic tablet substrates, and one such coated tablet is shown in photomicrograph B of FIG. 4. The mixing and spraying procedures for this coating are the same as those in Example 16.

HPMC/Polydextrose Formula

|  | % | Grams |
|---|---|---|
| HPMC | 38.28 | 11.48 |
| Polydextrose Powder | 23.08 | 6.92 |
| Titanium Dioxide | 29.70 | 8.91 |
| PEG 400 | 6.35 | 1.91 |
| FD&C Yellow No. 6, HT, 39% | 1.94 | 0.58 |
| D&C Yellow No. 10, HT, 17% | 0.65 | 0.20 |

As illustrated in photomicrograph A of FIG. 3, the film coating having no polydextrose in its coating formula did not adhere well to the tablet and is beginning to peel off or away from the tablet substrate. However, the film coating (photomicrograph B of FIG. 4) having polydextrose in its coating formula does adhere well to the tablet and is not peeling off the tablet substrate.

Example 30

A film coating based on the following HPMC/HPC formula is sprayed on hydrophobic tablet substrates, and one such coated tablet is shown below in photomicrograph C of FIG. 5. The mixing and spraying procedures for this coating are the same as those in Example 16.

HPMC/HPC Formula

|  | % | Grams |
|---|---|---|
| HPMC E-5 | 30.68 | 9.20 |
| Klucel EF | 30.68 | 9.20 |
| Titanium Dioxide | 29.70 | 8.91 |
| PEG 400 | 6.35 | 1.91 |
| FD&C Yellow No. 6, HT, 39% | 1.94 | 0.58 |
| D&C Yellow No. 10, HT 17% | 0.65 | 0.20 |

Figure 6:
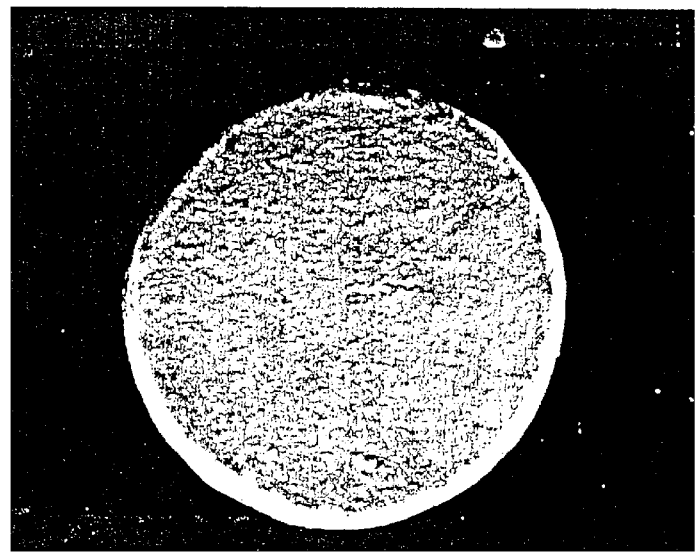
FIG. 6 shows photomicrograph D illustrating an HPMC/HPC/polydextrose formula film coating.

A film coating based on the following HPMC/HPC/Polydextrose formula is sprayed on hydrophobic tablet substrates, and one such coated tablet is shown in photomicrograph D of FIG. 6. The mixing and spraying procedures for this coating are the same as those in Example 16.

HPMC/HPC/Polydextrose Formula

|  | % | Grams |
|---|---|---|
| HPMC E-5 | 19.14 | 5.74 |
| Klucel EF | 19.14 | 5.74 |
| Polydextrose | 23.08 | 6.92 |
| Titanium Dioxide | 29.70 | 8.91 |
| PEG 400 | 6.35 | 1.91 |
| FD&C Yellow No. 6, HT, 39% | 1.94 | 0.58 |
| D&C Yellow No. 10, HT, 17% | 0.65 | 0.20 |

Figure 5:
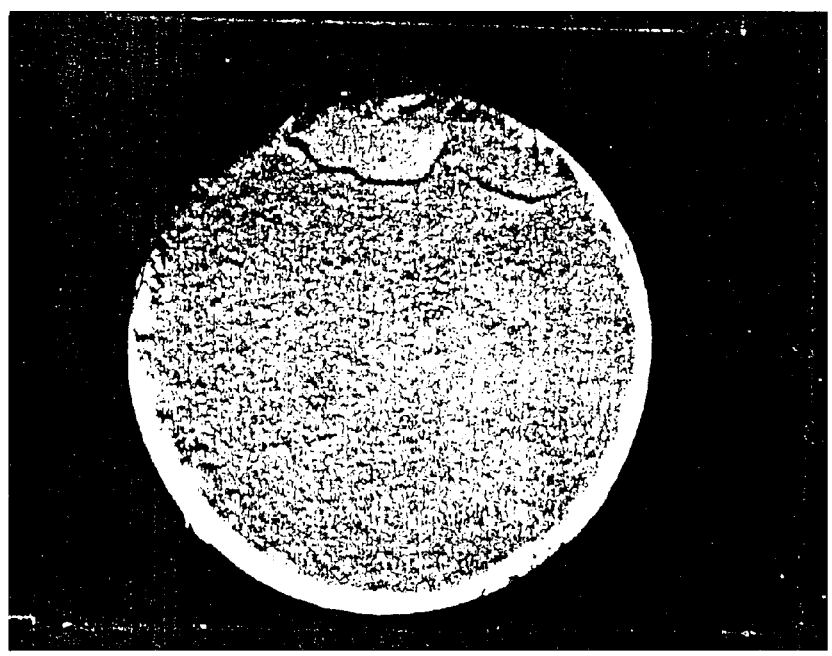
FIG. 5 shows photomicrograph C illustrating an HPMC/HPC formula film coating.

As illustrated in photomicrograph C of FIG. 5, the HPMC/HPC formula film coating does not adhere very well to the tablet. However, as shown in photomicrograph D of FIG. 6, the addition of polydextrose to the film coating improves adhesion of the film coating to the tablets.

Example 31

Figure 7:
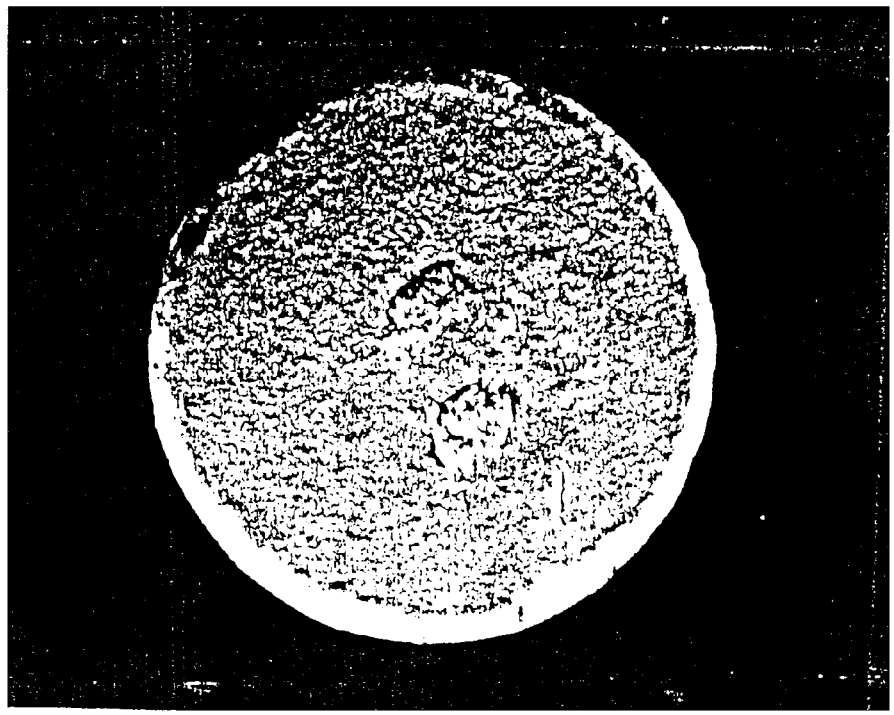
FIG. 7 shows a photomicrograph E illustrating an HPC formula film coating.

A film coating based on the following HPC formula is sprayed on hydrophobic tablet substrates, and one such coated tablet is shown in photomicrograph E of FIG. 7. The mixing and spraying procedures for this coating are the same as those in Example 16.

HPC/Formula

|  | % | Grams |
|---|---|---|
| Klucel EF | 61.36 | 18.40 |
| Titanium Dioxide | 29.70 | 8.91 |
| PEG 400 | 6.35 | 1.91 |
| FD&C Yellow No. 6, HT, 39% | 1.94 | 0.58 |
| D&C Yellow No. 10, HT, 17% | 0.65 | 0.20 |

Figure 8:
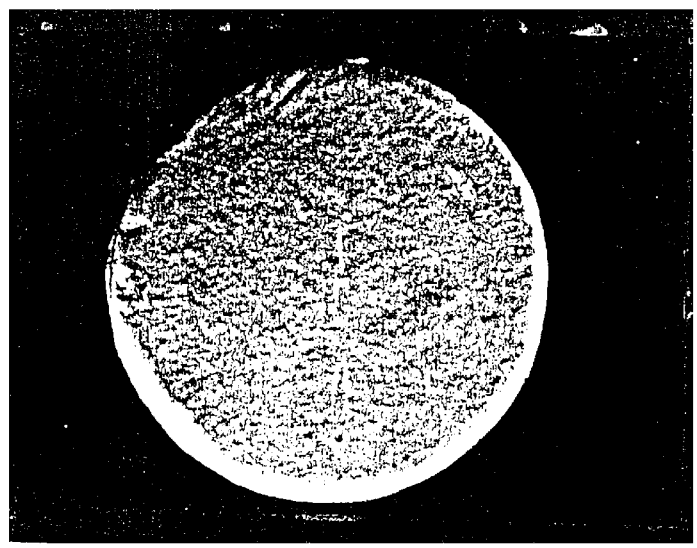
FIG. 8 shows a photomicrograph F illustrating an HPC/polydextrose formula film coating.

A film coating based on the following HPC/Polydextrose formula is sprayed on hydrophobic tablet substrates, and one such coated tablet is shown in photomicrograph F of FIG. 8. The mixing and spraying procedures for this coating are the same as those in Example 16.

HPC/Polydextrose Formula

|  | % | Grams |
|---|---|---|
| Klucel EF | 38.27 | 11.48 |
| Polydextrose | 23.08 | 6.92 |
| Titanium Dioxide | 29.70 | 8.91 |
| PEG 400 | 6.35 | 1.91 |
| FD&C Yellow No. 6, HT, 39% | 1.94 | 0.58 |
| D&C Yellow No. 10, HT, 17% | 0.65 | 0.20 |

As shown in photomicrograph E of FIG. 7, the HPC formula film coating having no polydextrose in its formula does not coat very well around the edges of the tablets, and this HPC formula film coating is very rough.

However, a comparison of the coated tablets shown in photomicrographs E (FIG. 7) and F (FIG. 8) shows that the HPC/Polydextrose formula coating adheres better than the HPC formula film coating. Further, the HPC/Polydextrose formula has a better appearance on the tablets than the HPC formula film coating does on the tablets.

Example 32

Figure 9:
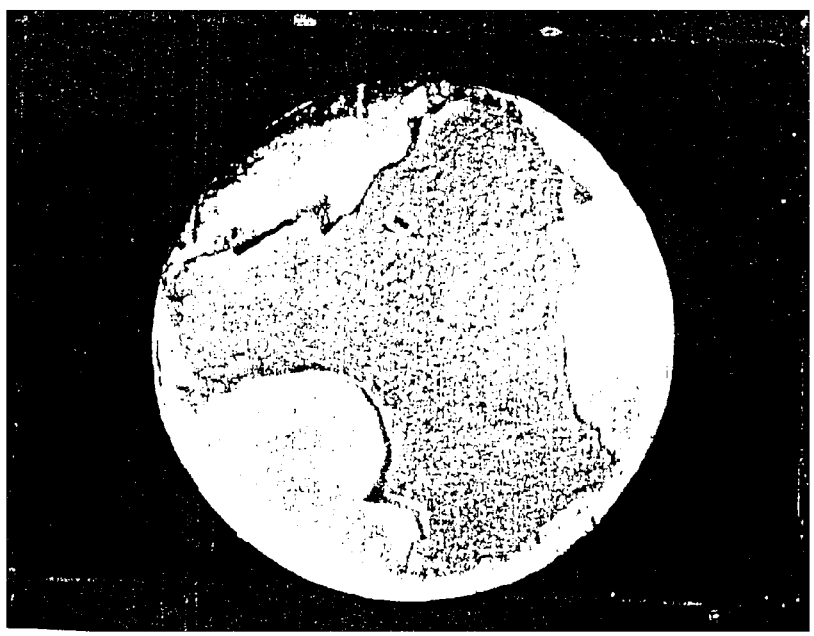
FIG. 9 shows a photomicrograph G illustrating an AQUACOAT formula film coating.

A film coating based on the following AQUACOAT formula is sprayed on hydrophobic tablet substrates, and one such coated tablet is shown in photomicrograph G of FIG. 9. The mixing and spraying procedures for this coating are the same as those in Example 18.

Aquacoat/Polydextrose Formula

|  | % | Grams |
|---|---|---|
| AQUACOAT (30% w/w) | 30.78 | 9.23 grams (dry solids) (30.77 grams as a solution) |
| HPMC E-5 (19% w/w) | 30.78 | 9.23 grams (dry solids) (48.60 grams as a solution) |
| Dibutyl Sebacate | 6.14 | 1.85 |
| Titanium Dioxide | 29.71 | 8.91 |
| FD&C Yellow No. 6, HT, 38% | 1.94 | 0.58 |

-continued

Aquacoat/Polydextrose Formula

|  | % | Grams |
| --- | --- | --- |
| D&C Yellow No. 10, HT, 15% | 0.65 | 0.20 |

Figure 10:
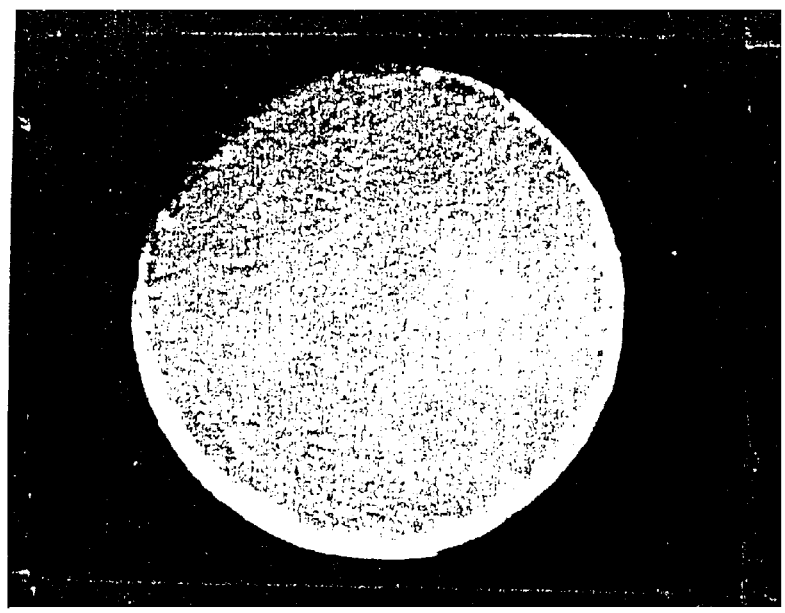
FIG. 10 shows a photomicrograph H illustrating an AQUACOAT/polydextrose formula film coating.

A film coating based on the following AQUACOAT/ Polydextrose formula is sprayed on hydrophobic tablet substrates, and one such coated tablet is shown in photomicrograph H of FIG. 10. The mixing and spraying procedures for this coating are the same as those in Example 18.

AQUACOAT/Polydextrose Formula

|  | % | Grams |
| --- | --- | --- |
| AQUACOAT (30% w/w) | 17.13 | 5.14 (dry solids) (17.23 as a solution) |
| HPMC E-5 | 17.13 | 5.14 (dry solids) (90.16 as a solution) |
| Polydextrose | 27.30 | 8.19 |
| Dibutyl Sebacate | 6.14 | 1.85 |
| Titanium Dioxide | 29.71 | 8.91 |
| FD&C Yellow No. 6, HT, 38% | 1.94 | 0.58 |
| D&C Yellow No. 10, HT, 15% | 0.65 | 0.20 |

As illustrated in photomicrograph G of FIG. 9, the film adhesion of the AQUACOAT formula film coating is very poor. However, as shown in photomicrograph H of FIG. 10, the addition of polydextrose to the film coating improves film adhesion.

Example 33

Figure 11:
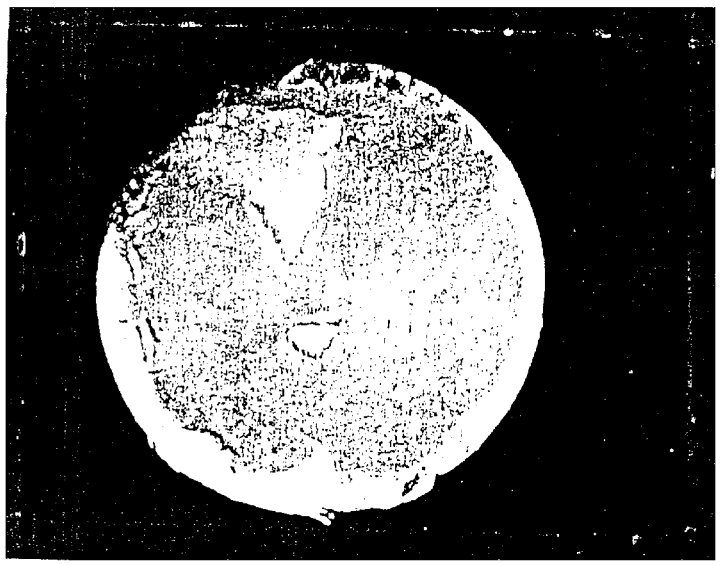
FIG. 11 shows a photomicrograph I illustrating a water soluble cellulose acetate formula film coating.

A film coating based on the following water-soluble cellulose acetate formula is sprayed on hydrophobic tablet substrates, and one such coated tablet is shown in photomicrograph I of FIG. 11. The mixing and spraying procedures are the same as those in Example 28.

Water-Soluble Cellulose Acetate Formula

|  | % | Grams |
| --- | --- | --- |
| Medium Viscosity Cellulose Acetate | 60.70 | 18.21 |
| Titanium Dioxide | 29.71 | 8.91 |
| Glycerine | 7.00 | 2.10 |
| FD&C Yellow No. 6, HT, 38% | 7.94 | 0.58 |
| D&C Yellow No. 10, HT, 15% | 1.94 | 0.20 |

Figure 12:
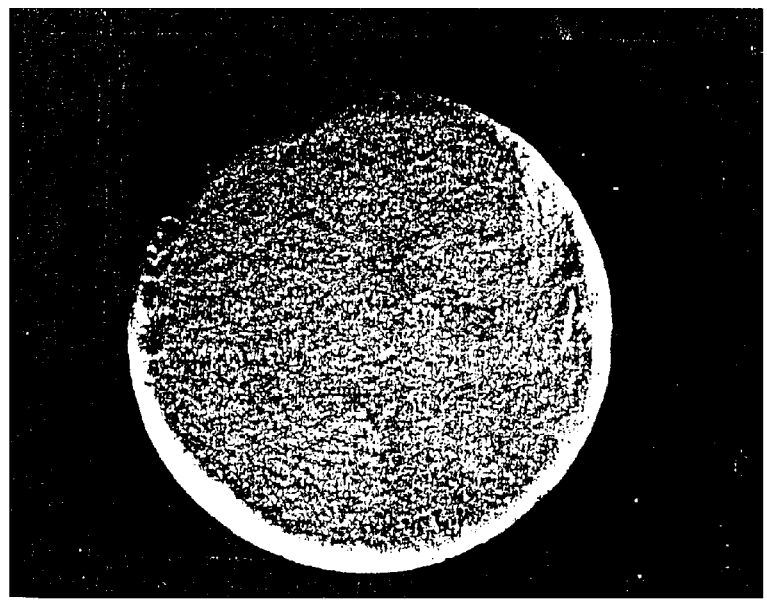
FIG. 12 shows a photomicrograph J illustrating a water-soluble cellulose acetate/polydextrose formula film coating.

A film coating based on the following water-soluble cellulose acetate/polydextrose formula is sprayed on hydrophobic tablet substrates, and one such coated tablet is shown in photomicrograph J of FIG. 12. The mixing and spraying procedures are the same as those in Example 28.

Water-Soluble Cellulose Acetate/Polydextrose Formula

|  | % | Grams |
| --- | --- | --- |
| Polydextrose | 23.08 | 6.92 |
| Medium Viscosity Cellulose Acetate | 37.62 | 11.28 |
| Titanium Dioxide | 29.71 | 8.91 |
| Glycerine | 7.00 | 2.10 |
| FD&C Yellow No. 6, HT, 38% | 1.94 | 0.58 |
| D&C Yellow No. 10, HT, 15% | 0.65 | 0.20 |

As shown in photomicrograph I of FIG. 11, the water-soluble cellulose acetate formula film coating does not adhere very well to the hydrophobic substrate. However, as illustrated in photomicrograph J of FIG. 12, the addition of polydextrose to the film coating improves film adhesion.

Example 34

Using the mixing and spraying procedures of Example 21, the following coatings are prepared and sprayed on hydrophobic tablet substrates.

Figure 13:
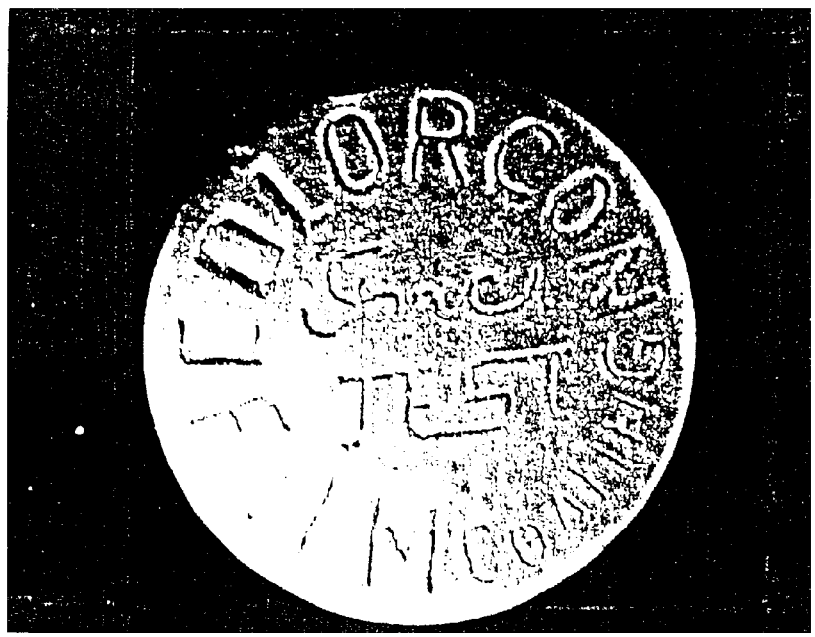
FIG. 13 shows a photomicrograph K illustrating an HPMC formula film coating (3% weight gain).

First, a film coating based on the following HPLC formula is sprayed on hydrophobic tablet substrates, and one such tablet is shown in photomicrograph K of FIG. 13. The average weight gain of the tablets is 3%.

HPMC/Formula

|  | % | Grams |
| --- | --- | --- |
| HPMC 6 cps | 69.51 | 34.75 |
| Titanium Dioxide | 11.59 | 5.79 |
| PEG 400 | 6.95 | 3.48 |
| FD&C Yellow No. 6, HT, 18% | 6.65 | 3.33 |
| D&C Yellow No. 10, HT 17% | 5.30 | 2.65 |

Figure 14:
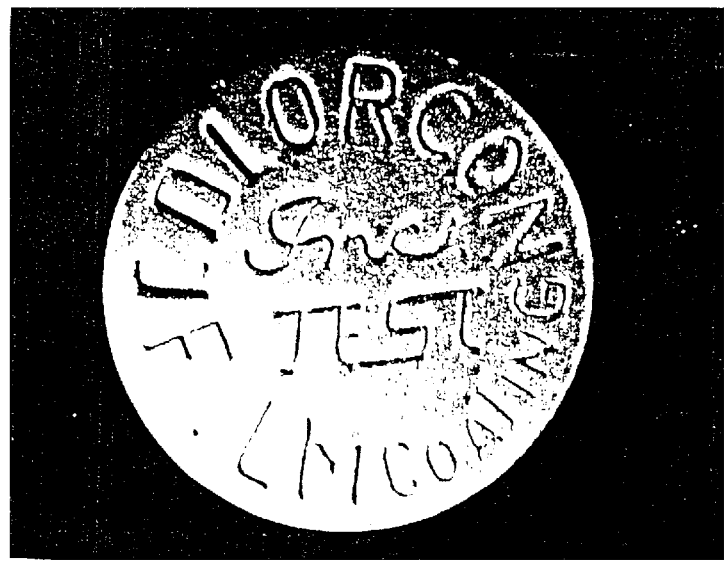
FIG. 14 shows a photomicrograph L illustrating an HPMC/polydextrose formula film coating (3% weight gain).

Second, a film coating based on the following HPLC/ Polydextrose formula is sprayed on hydrophobic tablet substrates, and one such coated tablet is shown in photomicrograph L of FIG. 14. The average weight gain of the tablets is 3%.

HPMC/Polydextrose Formula

|  | % | Grams |
| --- | --- | --- |
| HPMC 6 cps | 34.755 | 17.385 |
| Polydextrose | 34.755 | 17.385 |
| Titanium Dioxide | 11.59 | 5.79 |
| PEG 400 | 6.95 | 3.48 |
| FD&C Yellow No. 6, HT, 18% | 6.65 | 3.33 |
| D&C Yellow No. 10, HT 17% | 5.50 | 2.65 |

A comparison of photomicrographs K (FIG. 13) and L (FIG. 14) reveals that the addition of polydextrose to the film coating enhances the definition of the debossed logo on the tablets.

Figure 15:
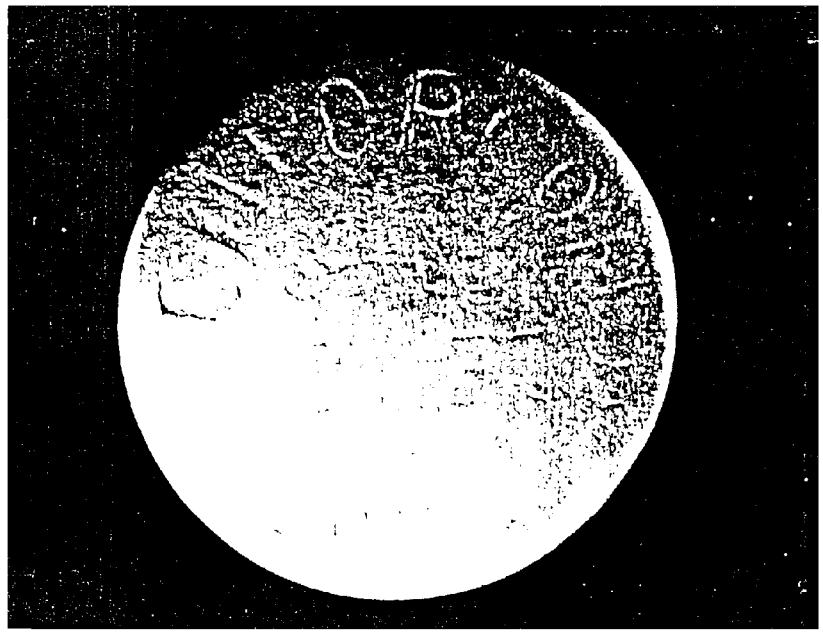
FIG. 15 shows a photomicrograph M illustrating an HPMC formula film coating (6% weight gain).

Photomicrograph M of FIG. 15 shows a hydrophobic tablet substrate coated with the HPLC formula film coating of this Example, but the weight gain of the tablet is 6%.

Figure 16:
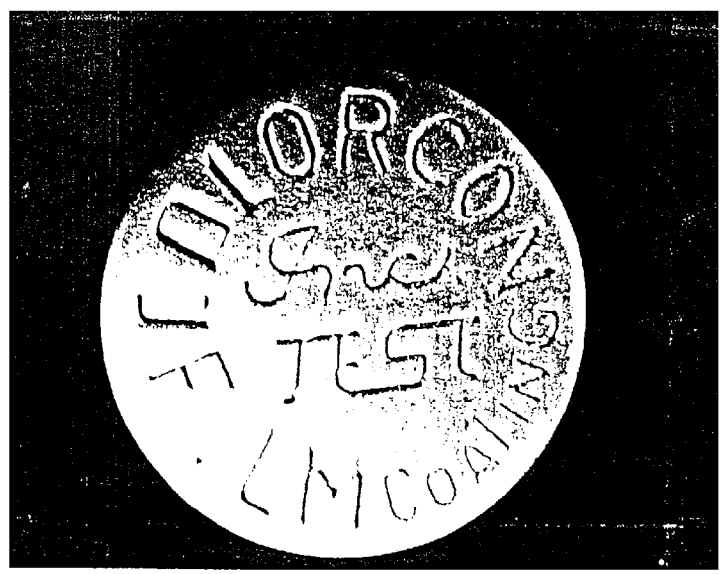
FIG. 16 shows a photomicrograph N illustrating an HPMC/polydextrose formula film coating (6% weight gain).

Photomicrograph N of FIG. 16 shows a hydrophobic tablet substrate coated with the HPLC/polydextrose formula film coating of this Example, but the weight gain of the tablet is 6%.

A comparison of photomicrographs M (FIG. 15) and N (FIG. 16) reveals that the addition of polydextrose to the film coating enhances the definition of the debossed logo on the tablets. Moreover, the addition of polydextrose to the film coating allows the definition of the debossed logo on the tablet to be crisper and clearer at higher percentage weight gains than the definition of the debossed logo on the tablet coated with the HPMC formula.

As illustrated in photomicrographs K (FIG. 13), L (FIG. 14), M (FIG. 15) and N (FIG. 16), the logo on the HPMC/polydextrose coated tablet remains clear and legible when the weight gain of the tablet is increased from 3% to 6%, whereas the logo on the HPMC coated tablet is unclear and illegible in part at a 6% weight gain (photomicrograph M of FIG. 15).

Example 35

In order to coat sunflower seeds (with shells), a formula having the following ingredients is mixed together by blending all dry ingredients together for approximately 30 seconds, adding the liquid ingredient, and blending for an additional 30 seconds. Then, 50 grams of the blended formula is dispersed into 283 grams of distilled water to make an aqueous coating suspension.

|  | % | Grams |
| --- | --- | --- |
| Polydextrose powder | 71.00 | 35.50 |
| PEG 400 | 2.26 | 1.13 |
| Alcolec F-100 | 2.26 | 1.13 |
| Sodium Alginate, Kelgin LV | 4.52 | 2.26 |
| Titanium dioxide | 10.00 | 5.00 |
| FD&C Yellow No. 5, HT, 16% | 10.00 | 5.00 |

One thousand grams of sunflower seeds having shells are sprayed in an AROMATIC spraying apparatus at 15% solids and 10 5.0% weight gain. The spray coating parameters are inlet air temperature 80° C., outlet air temperature 42° C., atomizing air 1.5 bar, and flowrate 12 grams/minute. The sunflower seeds having shells receive a nice coating.

Example 36

One thousand grams of sunflower seeds having shells are given a surcoat by being sprayed with a film coating having the following formula.

|  | % | Grams |
| --- | --- | --- |
| Polydextrose powder | 80.00 | 112.00 |
| Sodium alginate, Kelgin LV | 5.00 | 7.00 |
| PEG 400 | 2.50 | 3.50 |
| Alcolec F-100 | 2.50 | 3.50 |
| Titanium dioxide | 10.00 | 14.00 |

The mixing procedure for the formula is to blend all dry ingredients together for approximately 30 seconds, add the liquid ingredient, and then blend for an additional 30 seconds. Then, 140 grams of the blended formula is mixed with 60 grams of ARIEL 105. Then, 40 grams of the polydextrose/ARIEL 105 blended formula is dispersed into 270 grams of distilled water to form an aqueous coating suspension.

The aqueous coating suspension is sprayed on 1,000 grams of sunflower seeds having shells using an AROMATIC spraying apparatus. The spraying parameters are inlet air temperature 80° C., outlet air temperature 42° C., atomizing air 1.5 bar, and flowrate 12 grams/minute. The seeds are sprayed at 15% solids and at a 4% weight gain. The seeds are then sprayed in an AROMATIC spraying apparatus using the film coating suspension, procedures and conditions set forth in Example 35. The seeds receive a nice coating having good color.

Example 37

One thousand grams of sunflower seeds (without shells) are sprayed in an AROMATIC spraying apparatus with a film coating suspension that is based on the following formula at a 15% solids level and a 5% weight gain.

|  | % | Grams |
| --- | --- | --- |
| Polydextrose powder | 81.42 | 40.71 |
| Soda ash | 0.72 | 0.36 |
| Sodium alginate, Kelgin LV | 4.96 | 2.48 |
| Alcolec F-100 | 2.98 | 1.49 |
| Triacetin | 4.96 | 2.48 |
| PEG 8000 | 4.96 | 2.48 |

The formula is mixed together using the mixing feature of Example 35. Then, 50 grams of the blended formula is dispersed into 283 grams of distilled water to form an aqueous coating suspension. The spraying parameters are inlet air temperature 80° C., outlet air temperature 44° C., atomizing air 2.0 bar, and flowrate 12 grams/minute.

Example 38

Polydextrose may be combined with maltodextrin. As an example, a clear film coating suspension is prepared using the following formula.

|  | % | Grams |
| --- | --- | --- |
| Maltodextrin (Star Dri 1) | 47.45 | 23.72 |
| Polydextrose Powder | 25.55 | 12.78 |
| Triacetin | 10.00 | 5.00 |
| Sodium Alginate, Kelgin XL | 10.00 | 5.00 |
| Stearic Acid | 4.00 | 2.00 |
| Alcolec F-100 | 3.00 | 1.50 |

The formula is mixed using the mixing procedure of Example 35, and 10 grams of the blended maltodextrin/polydextrose formula is dispersed into 190 grams of distilled water to form an aqueous coating suspension. The maltodextrin/polydextrose aqueous film coating suspension is sprayed onto 1,000 grams of MCC/STARCH 1500 placebos at a 5.0% solids level and at a 1.0% weight gain. The spraying parameters are inlet air temperature 60° C., outlet air temperature 34° C., atomizing air 3.0 bar, and flowrate 12 grams/minute.

The maltodextrin is STAR DRI manufactured by A. E. Staley Manufacturing Co., Decateur, Ill.

Example 39

Another example of a clear film coating is prepared using the following formula.

|  | % | Grams |
|---|---|---|
| Maltodextrin (Star Dri 1) | 43.80 | 21.90 |
| Polydextrose powder | 29.20 | 14.60 |
| Propylene glycol alginate, Kelcoloid S | 10.00 | 5.00 |
| PEG 400 | 10.00 | 5.00 |
| Stearic Acid | 4.00 | 2.00 |
| Alcolec F-100 | 3.00 | 1.50 |

The mixing procedure for the formula is the same as that in Example 35.

Five grams of the blended formula is dispersed into 45 grams of distilled water to form a spraying solution, and using the same spraying parameters set forth in Example 38, the spraying solution is sprayed onto 1,000 grams of MCC/STARCH 1500 at a 10% solids level and at a 0.50% weight gain.

Example 40

Another example of a clear film coating is prepared using the following formula.

|  | % | Grams |
|---|---|---|
| Maltodextrin (Star Dri 1) | 29.20 | 14.60 |
| Polydextrose powder | 43.80 | 21.90 |
| Triacetin | 10.00 | 5.00 |
| HPMC E-50 | 10.00 | 5.00 |
| Stearic Acid | 4.00 | 2.00 |
| Alcolec F-100 | 3.00 | 1.50 |

The mixing procedure for the formula is the same as that in Example 35.

Ten grams of the blended formula is dispersed into 190 grams of distilled water to form a spraying solution, and using the same spraying parameters set forth in Example 38, the spraying solution is sprayed onto 1,000 grams of MCC/STARCH 1500 at a 5% solids level and at a 1.0% weight gain.

Example 41

Another example of a clear formula is as follows:

|  | % | Grams |
|---|---|---|
| Polydextrose powder | 19.50 | 9.75 |
| HPMC 6 cps | 45.50 | 22.75 |
| HPMC 3 cps | 20.00 | 10.00 |
| HPMC 50 cps | 5.00 | 2.50 |
| PEG 8000 | 5.00 | 2.50 |
| PEG 400 | 5.00 | 2.50 |

The mixing procedure for the formula is the same as that set out in Example 35.

Five grams of the blended formula is mixed into 95 grams of distilled water to form a spraying solution, and the spraying solution is sprayed onto 1000 grams of MCC/STARCH 1500 placebos at a 5% solids level and at a 0.50% weight gain. An AROMATIC spraying apparatus is used, and the spraying parameters are air inlet temperature 60° C., air outlet temperature 40° C., atomizing air 3.0 bar, and flow rate 8 grams/minute.

Example 42

Another example of a formula used for confectionery coatings is as follows.

|  | % | Grams |
|---|---|---|
| Maltodextrin (Star-Dri 1) | 41.75 | 83.50 |
| Polydextrose powder | 20.15 | 40.30 |
| Triacetin | 8.00 | 16.00 |
| Alcolec F-100 | 3.00 | 6.00 |
| Propylene glycol alginate, Kelcoloid S | 3.00 | 6.00 |
| Stearic Acid | 3.00 | 6.00 |
| Titanium dioxide | 4.50 | 9.00 |
| FD&C Yellow No. 5, 38%, HT | 10.75 | 21.50 |
| FD&C Yellow No. 5, 17%, HT | 5.85 | 11.70 |

The mixing procedure for this formula is the same as that in Example 35.

160 grams of blended formula is mixed into 906 grams of distilled water to form an aqueous spraying solution.

Eight kilograms of round chocolate pieces are placed in a 24 inch Accela-Cota coating pan, and the aqueous spraying solution is sprayed onto the chocolates. During the coating procedure, the inlet air is 36° C., the outlet air is 27° C., the atomizing air is 3 bar, the flow rate is 30 milliliters/minute, and the pan speed is 16 rpm. The chocolates are sprayed at a 15% solids level and at a 2% weight gain.

Example 43

Another example of a formula that is particularly adapted for applying a coating to chocolates and that includes polydextrose and maltodextrin is as follows.

|  | % | Grams |
|---|---|---|
| Maltodextrin | 39.93 | 79.86 |
| Polydextrose powder | 19.97 | 39.94 |
| Triacetin | 3.25 | 6.50 |
| PEG 8000 | 9.75 | 19.50 |
| Alcolec F-100 | 3.00 | 6.00 |
| Propylene glycol alginate, Kelcoloid S | 3.00 | 6.00 |
| Titanium Dioxide | 4.50 | 9.00 |
| FD&C Yellow No. 6, 38%, HT | 10.75 | 21.50 |
| FD&C Red No. 40, 38%, HT | 3.50 | 7.00 |
| FD&C Blue No. 2, 35%, HT | 2.35 | 4.70 |

The mixing and spraying procedures are the same as hose in Example 42.

Optimally, when using polydextrose with another polymer or polymers to form a film coating, the total amount of polymer including the polydextrose is 60 to 70% of the blended formula and polydextrose is 30 to 50% of the 60–70%.

Advantages

The polydextrose coatings of the invention have the advantage of adhering to surfaces that are difficult to coat, such as the waxy matrix surfaces of some pharmaceutical tablets, such as Dimetaps. The coatings also have the further advantage of adhering to the debased or intaglio surfaces of logos or words on tablets without obscuring those logos or words. This is very important when a manufacturer debosses his trademark, which may be a design or words, on his product. Previously, coatings made of. cellulosic polymer film formers would bridge the grooves formed by the debased word or design on the tablet, and would obscure it so that it could not be read.

In addition to coating waxy matrix tablets, the polydextrose coating of the invention is particularly adapted to coat sugarless chewing gum pieces which are very difficult to coat in an aqueous system. The coating suspension of Example 3 is particularly effective in coating sorbitol gum pieces.

Adding polydextrose to conventional film formers to form a film coating increases adhesion of the film coating. For example, use of polydextrose with hydroxypropyl methylcellulose (HPLC) in a film coating may double or triple adhesion compared to the adhesion value with use of HPLC alone. Further, adding polydextrose to conventional film formers increases color stability in accelerated light conditions compared with use of a conventional film former alone.

Use of polydextrose as a film former in a film coating leads to lower costs since it is cheaper than cellulosic film formers. Further, a film coating suspension having polydextrose may be sprayed effectively at a higher percentage solids level than a film coating suspension based on a conventional film former having no polydextrose, which results in shorter spraying times and an increase in productivity.

What is claimed is:

1. A method of film coating solid forms such as pharmaceutical tablets, food, confectionery forms, seeds for agriculture, and the like with a protective film comprising the steps of
    mixing an effective amount of film forming polydextrose, an effective amount of plasticizer, an effective amount of detackifier, and an effective amount of secondary film former into water to form an aqueous coating suspension,
    forming a film coating on the solid forms by applying an effective amount of said coating suspension onto said solid forms to form a film coating thereon, and
    drying the film coating on said solid forms.
2. The method of claim 1, including
    dispersing a colorant in the coating suspension before applying the coating suspension to the solid forms.
3. The method of claim 1, wherein
    the plasticizer is polyethylene glycol, triacetin, propylene glycol, acetyltriethyl citrate, dibutyl sebacate, or glycerine, or a mixture thereof.
4. The method of claim 1, wherein
    the plasticizer is in a range of 2.5% to 10% by weight of the non-water ingredients of the aqueous coating suspension.
5. The method of claim 1, wherein
    the detackifier is lecithin or mineral oil.
6. The method of claim 1, wherein
    the detackifier is in the range of 1% to 3% by weight of the non-water ingredients of the aqueous coating suspension.
7. The method of claim 1, wherein
    the secondary film former is sodium alginate or propylene glycol alginate.
8. The method of claim 1, wherein
    the secondary film former is in the range of 2% to 10% by weight of the non-water ingredients of the aqueous coating suspension.
9. The method of claim 2, wherein
    said colorants are FD&C lakes, D&C lakes, titanium dioxide, or FD&C or D&C dyes.
10. The method of claim 2, wherein
    said colorants are in the range of 0% to 25% by weight of the non-water ingredients of the aqueous coating suspension.
11. The method of claim 2,
    the plasticizer being polyethylene glycol, triacetin, propylene glycol, acetyltriethyl citrate, dibutyl sebacate, or glycerine, or a mixture thereof,
    the detackifier being lecithin or mineral oil,
    the secondary film former being sodium alginate or propylene glycol alginate,
    and the colorants being FD&C lakes, D&C lakes, titanium dioxide, or FD&C or D&C dyes.
12. The method of claim 1,
    the polydextrose being 30 to 90% by weight of the non-water ingredients of the aqueous coating suspension,
    dispersing a colorant in the coating suspension before applying the coating suspension to the solid forms,
    the colorants being FD&C lakes, D&C lakes, titanium dioxide, or FD&C or D&C dyes, and being 0 to 25% by weight of the non-water ingredients of the suspension,
    the plasticizer being polyethylene glycol, triacetin, propylene glycol, acetyltriethyl citrate, dibutyl sebacate, or glycerine, or a mixture thereof, in a range of 2.5% to 20% by weight of the non-water ingredients of the suspension,
    the detackifier being lecithin or mineral oil in a range of 1 to 3% by weight of the non-water ingredients of the aqueous coating suspension, and
    the secondary film former being sodium alginate or propylene glycol alginate in a range of 2% to 10% by weight of the non-water ingredients of the aqueous coating suspension.
13. A method of film coating solid forms such as pharmaceutical tablets, food, confectionery forms, seeds for agriculture, and the like with a protective film comprising the steps of
    mixing an effective amount of film forming polydextrose, an effective amount of plasticizer, an effective amount of detackifier, and an effective amount of secondary film former into water to form an aqueous coating suspension,
    said solid forms having debased words or designs on their outer surface,
    forming a film coating on the solid forms by applying an effective amount of said coating suspension onto said solid forms to form a film coating thereon without obscuring the debased words or designs by bridging, and
    drying the film coating on said solid forms.
14. A method of film coating solid forms such as pharmaceutical tablets, food, confectionery forms, seeds for agriculture, and the like with a protective film comprising the steps of
    mixing effective amounts of film forming polydextrose, plasticizer, and a second polymer into water to form an aqueous coating suspension, forming a film coating on the solid forms by applying an effective amount of said coating suspension onto said solid forms to form a film coating thereon, and drying the film coating on said solid forms.

15. The method of claim 14, the second polymer being a cellulosic polymer.

16. The method of claim 15, the cellulosic polymer being hydroxypropyl methylcellulose, hydroxypropyl cellulose, pseudolatex ethylcellulose, or water-soluble cellulose acetate.

17. The method of claim 14, the second polymer being an acrylic polymer.

18. The method of claim 17, the acrylic polymer being an acrylic latex.

19. The method of claim 14, the second polymer being maltodextrin.

20. The method of claim 14, including mixing a detackifier into said aqueous coating suspension.

21. The method of claim 14, including dispersing a colorant in the coating suspension before applying the coating suspension onto the tablets.

22. The method of claim 14, wherein the plasticizer is polyethylene glycol, triacetin, propylene glycol, acetyltriethyl citrate, dibutyl sebacate, or glycerine, or a mixture thereof.

23. The method of claim 14, wherein the plasticizer is in a range of 2.5% to 20% by weight of the aqueous coating suspension without the water.

24. The method of claim 20, the detaclkifier being lecithin or mineral oil.

25. The method of claim 20, wherein the detackifier is in the range of 1% to 3% by weight of the non-water ingredients of the aqueous coating suspension.

26. The method of claim 21, wherein said colorants are FD&C lakes, D&C lakes, titanium dioxide, or FD&C or D&C dyes.

27. The method of claim 21, wherein said colorants are in the range of 0% to 53% by weight of the non-water ingredients of the aqueous coating suspension.

28. The method of claim 14, including mixing a secondary film former into said aqueous coating suspension.

29. The method of claim 28, the secondary film former being sodium alginate or propylene glycol alginate.

30. A method of film coating solid forms such as pharmaceutical tablets, food, confectionery forms, seeds for agriculture, and the like with a protective film comprising the steps of mixing together effective amounts of film forming polydextrose, plasticizer, detackifier, secondary film former, and a second polymer into water to form an aqueous coating suspension, forming a first film coating on the solid forms by applying an effective amount of said coating suspension onto said solid forms to form a film coating thereon, drying the first film coating on said tablets, forming a second film coating on the solid forms by applying an effective amount of a coating solution onto the solid forms to overcoat said first film coating and form the second film coating thereon, and drying the second film coating on said solid forms.

31. The method of claim 30, the second thin polymeric coating solution and polymeric film coating being made from a cellulosic polymer.

32. The method of claim 31, the cellulosic polymer being hydroxypropyl methylcellulose, hydroxypropyl cellulose, pseudolatex ethylcellulose, or water-soluble cellulose acetate.

33. The method of claim 30, including dispersing colorant in the polymeric coating solution before spraying it onto said solid forms.

34. A method of film coating solid forms such as pharmaceutical tablets, food, confectionery forms, seeds for agriculture, and the like with a protective film comprising the steps of mixing an effective amount of a primary film-former comprising polydextrose and a second polymer together with effective amounts of a plasticizer, a detackifier, and a secondary film-former into water to form an aqueous coating suspension, the polydextrose being greater than 0% by weight of the primary film former, forming a film coating on the solid forms by applying an effective amount of said coating suspension onto said solid forms to form a film coating thereon, and drying the film coating on said solid forms.

35. The method of claim 34, the second polymer being a cellulosic polymer.

36. The method of claim 35, the cellulosic polymer being hydroxypropyl methylcellulose, hydroxypropyl cellulose, pseudolatex ethylcellulose, or water-soluble cellulose acetate.

37. The method of claim 34, the second polymer being an acrylic polymer.

38. The method of claim 37, the acrylic polymer being an acrylic latex.

39. The method of claim 34, the second polymer being maltodextrin.

40. The method of claim 34 including dispersing a colorant in the coating suspension before applying the coating suspension onto the tablets.

41. The method of claim 40, wherein said colorants are FD&C lakes, D&C lakes, titanium dioxide, or FD&C or D&C dyes.

42. The method of claim 40, wherein said colorants are in the range of 0% to 53% by weight of the non-water ingredients of the aqueous coating suspension.

43. The method of claim 34, wherein the plasticizer is polyethylene glycol, triacetin, propylene glycol, acetyltrietliyl citrate, dibutyl sebacate, or glycerine, or a mixture thereof.

44. The method of claim 34, wherein the plasticizer is in a range of 2.5% to 20% by weight of the aqueous coating suspension without the water.

45. The method of claim 34, the detackifier being lecithin or mineral oil.

46. The method of claim 34, wherein the detackifier is in the range of 1 to 3% by weight of the non-water ingredients of the aqueous coating suspension.

47. The method of claim 34, wherein
the secondary film former being sodium alginate or propylene glycol alginate.

48. The product made in accordance with the method of claim 1.

49. The product made in accordance with the method of claim 11.

50. The product made in accordance with the method of claim 12.

51. The product made in accordance with the method of claim 13.

52. The product made in accordance with the method of claim 14.

53. The product made in accordance with the method of claim 29.

54. The product made in accordance with the method of claim 34.

55. A method of film coating solid forms such as pharmaceuticals tablets, food, comfectionary forms seeds for agriculture, and the like with a protective film comprising the steps of mixing a primary film-former comprising polydextrose and a second polymer, together with a plasticizer, a detackifier, a secondary film former, and colorant into water to form an aqueous coating suspension, the primary film-former being in a range of 60% to 70% by weight of the non-water ingredients of the aqueous coating suspension, the polydextrose being in a range of 30% to 50% by weight of the primary film former, the second polymer being pseudolatex ethylcellulose, water-soluble cellulose acetate, acrylic latex, or maltodextrin, the plasticizer being polyethylene glycol, triacetin, propylene gylcol, acetryltriethyl citarate, dibutyl sebacate, or glycerine, or a mixture thereof, the plasticizer being in a range of 2.5% to 20% by weight of the aqueous coating suspension without the water, the secondary film former being sodium alginate or propylene glycol alginate, the secondary film former being in a range of 0% to about 10% by weight of the non-water ingredients of the aqueous coating suspension, the detackifier being lecithin or mineral oil, the detackifier being in a range of 0% to about 3% by weight of the non-water ingredients of the aqueous coating suspension, the colorants being FD&C lakes, D&C lakes, titanium dioxide, or the colorants being in a range of 0% to about 33% by weight of the non-water ingredients of the aqueous coating suspension, forming a film coating on the solid forms by applying an effective amount of said coating suspension onto said solid forms to form a film coating thereon, and drying the film coating on said solid forms.

* * * * *